United States Patent [19]

Toda et al.

[11] Patent Number: 5,486,556
[45] Date of Patent: Jan. 23, 1996

[54] POLYMER COMPOSITION CONTAINING A PIPERIDYL-TRIAZINE COMPOUND

[75] Inventors: Toshimasa Toda; Satoru Naito; Hisayu Osawa; Takaaki Yamazaki, all of Tokyo, Japan

[73] Assignee: Sankyo Company, Limited, Tokyo, Japan

[21] Appl. No.: 432,665

[22] Filed: May 2, 1995

Related U.S. Application Data

[62] Division of Ser. No. 474,292, Feb. 2, 1990, Pat. No. 5,446,144, which is a continuation of Ser. No. 257,753, Oct. 14, 1988, abandoned.

[30] Foreign Application Priority Data

Oct. 30, 1987 [JP] Japan ................. 62-273138

[51] Int. Cl.$^6$ ................................ C08K 5/3492
[52] U.S. Cl. .................................... 524/100
[58] Field of Search ............................... 524/100

[56] References Cited

U.S. PATENT DOCUMENTS

| | | | |
|---|---|---|---|
| 4,108,829 | 8/1978 | Cassandrini et al. | 544/198 |
| 4,288,593 | 9/1981 | Rody | 544/198 |
| 4,321,374 | 4/1982 | Morimura et al. | 544/198 |
| 4,400,505 | 8/1983 | Loffelman et al. | 544/198 |
| 4,415,689 | 11/1983 | Minagawa et al. | 524/100 |
| 4,433,145 | 2/1984 | Wiezer et al. | 544/198 |
| 4,461,861 | 7/1984 | Loffelman et al. | 544/198 |
| 4,698,381 | 10/1987 | Minagawa et al. | 524/100 |
| 4,716,187 | 12/1987 | Avar | 524/99 |

FOREIGN PATENT DOCUMENTS

| | | |
|---|---|---|
| 0022080 | 1/1981 | European Pat. Off. . |
| 0109937 | 5/1984 | European Pat. Off. . |
| 0209126 | 1/1987 | European Pat. Off. . |
| 3111209 | 9/1982 | Germany . |
| 62-63570 | 3/1987 | Japan . |
| 176662/86 | 8/1988 | Japan . |

*Primary Examiner*—Kriellion S. Morgan
*Attorney, Agent, or Firm*—Frishauf, Holtz, Goodman, Langer & Chick

[57] ABSTRACT

A polymer composition comprising a polymer stabilized against the effects of light and heat by the incorporation of a polymer stabilizer, wherein the polymer stabilizer comprises at least one compound selected from the group consisting of compounds of formula (I):

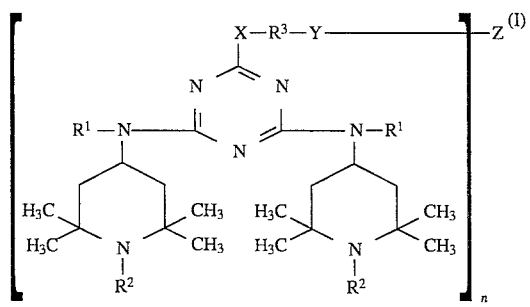

wherein $R^1$ is hydrogen, alkyl, alkoxyalkyl, carboxylic acyl or phenylalkyl, or an optionally substituted tetramethylpiperidyl group; $R^2$ is hydrogen, alkyl, carboxylic acyl or phenylalkyl group; $R^3$ is alkylene optionally interrupted by at least one oxygen atom; X is oxygen or —$NR^5$—, wherein $R^5$ is hydrogen or alkyl; Y is —OCO—, —COO—, —CONH— or —OCONH—; n is 2 to 4; and, when n is 2, Z is alkylene optionally interrupted by at least one oxygen, or sulfur or aryl, cycloalkyl or heterocyclic group, or, when n is 3, Z is alkanetriyl in which a carbon is optionally replaced by nitrogen or, when n is 4, Z is alkanetetrayl optionally interrupted by at least one oxygen atom, and acid addition salts of such compounds.

10 Claims, No Drawings

POLYMER COMPOSITION CONTAINING A PIPERIDYL-TRIAZINE COMPOUND

This is a division of application Ser. No. 07/464,292 filed Feb. 2, 1990 now U.S. Pat. No. 5,6,144, which is a continuation of application Ser. No. 07/257,753 filed Oct. 14, 1988 now abn.

BACKGROUND TO THE INVENTION

The present invention relates to a series of novel piperidyl-triazine derivatives which are useful as stabilizers for synthetic polymers.

In recent years, a number of triazine derivatives have been proposed for use as polymer stabilizers, for example as disclosed in U.S. Pat. No. 4,108,829, No. 4,433,145, No. 4,400,505 and No. 4,461,861 and in Japanese Patent Application Kokai (i.e. as laid open to public inspection) No. 176 662/86. Of these, the closest prior art is believed to be Japanese Application Kokai No. 176 662/86, which discloses, inter alia, the compound 1,3-bis<3-{2,4-bis[N-butyl-N-(2,2,6,6-tetramethyl-4-piperidyl)amino] -1,3,5-triazin-6-ylamino}propoxy>-2,2-dimethylpropane and proposes its use as a polymer stabilizer.

In broad, general terms, the chemical structure of these prior art compounds, including that one specifically mentioned above, insofar as they are relevant to the compounds of the present invention, may be described as having a piperidylaminotriazinyl group attached via, for example, an amino group to an alkylene group, which itself may optionally be interrupted by certain specific atoms or groups. In the case of the prior art compounds, the alkylene group is interrupted by certain specific atoms or groups, such as an oxygen or sulfur atom or an amino group.

We have now surprisingly discovered a series of piperidyl-triazine derivatives in which the alkylene group is interrupted by a group of formula —OCO—, —COO—, —CONH— or —OCONH—, which is unusual in this type of compound. These compounds have a very low volatility, and indeed, do not even volatilize to any great extent when the polymer containing them is heated. Moreover, they result in little blooming and additionally are excellent polymer stabilizers against heat and light.

The only compounds of this type that we have been able to discover having an alkylene group interrupted by groups similar to those in the present invention are disclosed in Japanese Patent Application Kokai No. 63570/87 and in United Kingdom Patent No. 2 136 805. Although these prior compounds are disclosed for use as polymer stabilizers, they differ from the compounds of the present invention in that they have a piperidylamino group attached directly to the alkylene group and lack the triazine group of the present invention. The compounds of the present invention have been found to be significantly more effective polymer stabilizers than these prior compounds.

BRIEF SUMMARY OF THE INVENTION

The novel piperidyl-triazine derivatives of the present invention can be represented by the following formula (I):

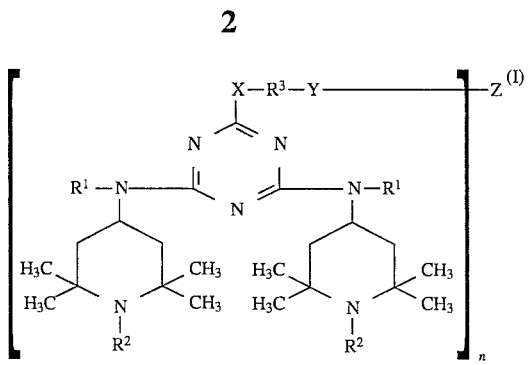

wherein:

$R^1$ represents a hydrogen atom, an alkyl group having from 1 to 18 carbon atoms, an alkoxyalkyl group having from 3 to 22 carbon atoms, a carboxylic acyl group having from 2 to 18 carbon atoms, a phenylalkyl group in which the alkyl part has from 1 to 4 carbon atoms and in which the phenyl part is unsubstituted or has at least one substituent selected from the group consisting of $C_1$–$C_4$ alkyl groups, $C_1$–$C_4$ alkoxy groups and halogen atoms, or a group of formula (II):

wherein $R^4$ has the same meaning as defined below $R^2$;

$R^2$ represents a hydrogen atom, an alkyl group having from 1 to 18 carbon atoms, a carboxylic acyl group having from 2 to 18 carbon atoms or a phenylalkyl group in which the alkyl part has from 1 to 4 carbon atoms and in which the phenyl part is unsubstituted or has at least one substituent selected from the group consisting of $C_1$–$C_4$ alkyl groups, $C_1$–$C_4$ alkoxy groups and halogen atoms;

$R^3$ represents an alkylene group having from 1 to 6 carbon atoms or an alkylene group having from 1 to 6 carbon atoms which is interrupted by at least one oxygen atom;

X represents an oxygen atom or a group of formula —$NR^5$—, wherein $R^5$ represents a hydrogen atom or an alkyl group having from 1 to 4 carbon atoms:

Y represents a group of formula —OCO—, a group of formula —COO—, a group of formula —CONH— or a group of formula —OCONH—;

n is an integer from 2 to 4; and when n is 2:

Z represents:

(i) an alkylene group having from 1 to 18 carbon atoms or an alkylene group having from 1 to 18 carbon atoms which is interrupted by at least one member selected from the group consisting of oxygen atoms, sulfur atoms and groups of formula (II'):

or (ii) a group of formula (III):

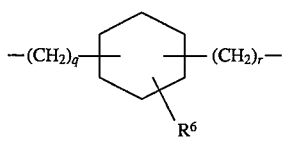

or (iii) a group of formula (IV):

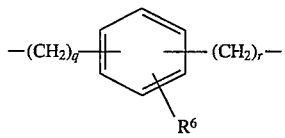

or (iv) a group of formula (V):

or (v) a group of formula (VI):

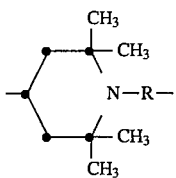

wherein:

$R^6$ represents a hydrogen atom or an alkyl group having from 1 to 4 carbon atoms;

R represents an alkylene group having from 2 to 4 carbon atoms;

p is an integer from 1 to 4; and q and r are independently selected from the group consisting of the cipher 0 and the integers from 1 to 3;

when n is 3:

Z represents an alkanetriyl group having from carbon atoms or a group of formula (VII):

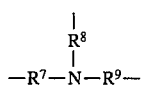

wherein $R^7$, $R^8$ and $R^9$ are independently selected from the group consisting of alkylene groups having from 1 to 5 carbon atoms, provided that the total number of carbon atoms in $R^7+R^8+R^9$ is from 3 to 8;

or when n is 4:

Z represents an alkanetetrayl group having from 4 to 8 carbon atoms or an alkanetetrayl group having from 4 to 8 carbon atoms which is interrupted by at least one oxygen atom;

and acid addition salts thereof.

The invention further provides a polymer, preferably a synthetic polymer, composition comprising a polymer stabilized against the effects of light and heat by the incorporation of a polymer stabilizer, wherein the polymer stabilizer comprises at least one compound selected from the group consisting of compounds of formula (I) and acid addition salts thereof.

The invention also provides processes for preparing the compounds of the present invention, which processes are described in more detail hereafter.

DETAILED DESCRIPTION OF INVENTION

Where $R^1$ represents an alkyl group having from 1 to 18 carbon atoms, this can be a straight or branched chain group, and examples include the methyl, ethyl, propyl, isopropyl, butyl, hexyl, octyl, 2-ethylhexyl, decyl, dodecyl and octadecyl groups. Of these, we prefer those alkyl groups having from 1 to 8 carbon atoms.

Where $R^1$ represents an alkoxyalkyl group having from 3 to 22 carbon atoms, we prefer that the alkoxy moiety should have from 1 to 18 carbon atoms and the alkyl moiety should have from 2 to 4 carbon atoms. Examples of alkoxy groups having from 1 to 18 carbon atoms include the methoxy, ethoxy, propoxy, isopropoxy, butoxy, hexyloxy, octyloxy, 2-ethylhexyloxy, decyloxy, dodecyloxy and octadecyloxy groups. Of these, we prefer those alkoxy groups having from 1 to 8 carbon atoms, for example, the methoxy, ethoxy, propoxy, isopropoxy, butoxy, hexyloxy and octyloxy groups. Examples of alkyl groups having from 2 to 4 carbon atoms include the ethyl, propyl, isopropyl, butyl and isobutyl groups, of which the ethyl group is preferred.

Where $R^1$, $R^2$ or $R^4$ represents a carboxylic acyl group having from 2 to 18 carbon atoms, this is preferably an alkanoyl or alkenoyl group having up to 18 carbon atoms in a straight or branched chain (for example, an acetyl, propionyl, acryloyl, butyryl, hexanoyl, octanoyl, lauroyl, palmitoyl or stearoyl group) or an arylcarbonyl group in which the aryl group has from 6 to 10 ring atoms and is unsubstituted or has at least one substituent selected from the group consisting of $C_1$–$C_4$ alkyl groups (i.e. the methyl, ethyl, propyl, isopropyl, butyl, isobunyl, sec-butyl and t-butyl groups, preferably the methyl group), $C_1$–$C_4$ alkoxy groups (e.g. the methoxy, ethoxy, propoxy, isopropoxy, butoxy, isobutoxy and sec-butoxy groups, preferably the methoxy group) and halogen atoms (i.e. fluorine, chlorine, bromine and iodine atoms, preferably the fluorine and chlorine atoms); examples of such arylcarbonyl groups include the benzoyl group and substituted equivalents thereof. Of these we prefer the aliphatic carboxylic acyl groups having from 2 to 4 carbon atoms, most preferably the acetyl group.

Where $R^1$, $R^2$ or $R^4$ represents a phenylalkyl group, this may be unsubstituted or substituted, as defined above. The alkyl part of the phenylalkyl group has from 1 to 4 carbon atoms, and examples include the methyl, ethyl, propyl, isopropyl, butyl and isobutyl groups. Where the group is substituted, there may be a single substituent or 2 or more substituents, and, where there are 2 or more substituents, these may be the same or different, and are preferably on the aryl moiety. Examples of such phenylalkyl groups include the benzyl, phenethyl, p-methylbenzyl and p-chlorobenzyl groups, of which the benzyl group is preferred.

Where $R^2$ or $R^4$ represents an alkyl group having from 1 to 18 carbon atoms, this may be any one of the groups exemplified above for the alkyl group of $R^1$. In this case, the group is preferably an alkyl group having from 1 to 4 carbon atoms, for example, a methyl, ethyl, propyl, isopropyl or butyl group, of which the methyl group is preferred.

Where $R^3$ represents an alkylene group having from 1 to 6 carbon atoms or an alkylene group having from 1 to 6 carbon atoms which is interrupted by an oxygen atom, this may be, for example, a methylene, ethylene, ethylidene, propylene, trimethylene, isopropylidene, tetramethylene, pentamethylene, hexamethylene or 3-oxapentamethylene group. Of these, we prefer the $C_1$–$C_4$ alkylene groups, more preferably the methylene or ethylene group.

When n is 2, Z may represent an alkylene group having from 1 to 18 carbon atoms in which the carbon chain may optionally be interrupted by an oxygen atom, by a sulfur atom or by a group of formula (II'), as defined above. Examples of such groups which may be represented by Z include the methylene, ethylene, trimethylene, propylene, tetramethylene, 3-methyltrimethylene, pentamethylene, 2,2-dimethyltrimethylene, hexamethylene, heptamethylene, octamethylene, decamethylene, dodecamethylene and hexadecamethylene groups, as well as groups of formulae:
—$(CH_2)_2$—O—$(CH_2)_2$—,  —$(CH_2)_2$—S—$(CH_2)_2$—,
—$(CH_2)_2$—O—$(CH_2)_2$—,  —$(CH_2)_3$—O—$(CH_2)_3$—,
—$(CH_2)_2$—O—Ph(1,4)—O—$(CH_2)_2$—O—Ph(1,3)—O—$(CH_2)_2$—, and —$(CH_2)_4$—O—Ph(1,4)—O—$(CH_2)_4$—, where Ph(1,3) and Ph(1,4) stand for the 1,3- and 1,4-phenylene groups, respectively. Of these, those alkylene groups having from 2 to 8 carbon atoms are preferred.

Where $R^5$ or $R^6$ represents an alkyl group having from 1 to 4 carbon atoms, this may be a straight or branched chain group and examples include the methyl, ethyl, propyl, isopropyl, butyl, isobutyl, sec-butyl and t-butyl groups, of which the methyl group is preferred.

Where R represents an alkylene group having from 2 to 4 carbon atoms, this may be a straight or branched chain group and the "free" valencies may be attached to the same carbon atom or to different carbon atoms. Examples include the ethylene, ethylidene, propylene, isopropylidene, trimethylene and tetramethylene groups, of which the $C_2$ and $C_3$ groups are preferred.

When n is 3, Z may represent an alkanetriyl group having from 3 to 8 carbon atoms or a group of formula (VII), defined above. Examples of such groups include those having the formulae:

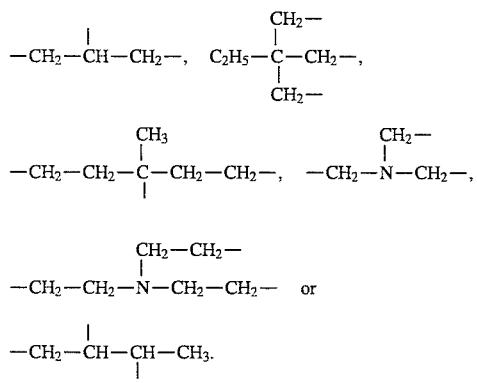

Of these, we especially prefer those groups having the following formula:

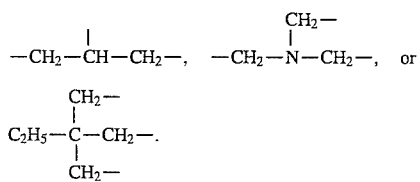

When n is 4, Z may represent an alkanetetrayl group having from 4 to 8 carbon atoms which may optionally be interrupted by an oxygen atom. Examples include groups of the following formula:

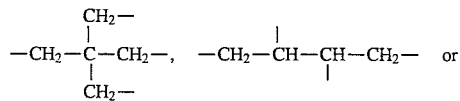

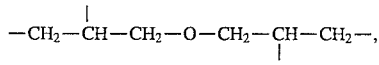

and preferably a group of the following formula:

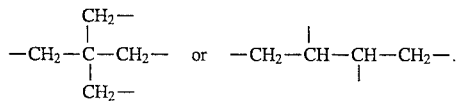

The compounds of the present invention necessarily include within their molecular structure at least 4 groups represented by $R^1$ and by $R^2$; these groups may be the same or different from each other. In general, it is convenient and easy to prepare compounds where all groups $R^1$ are the same and all groups $R^2$ are the same, and these are, therefore, preferred. However, compounds in which some or all of these groups are different are also part of the present invention. Likewise, the compounds necessarily contain at least 2 groups of formula:

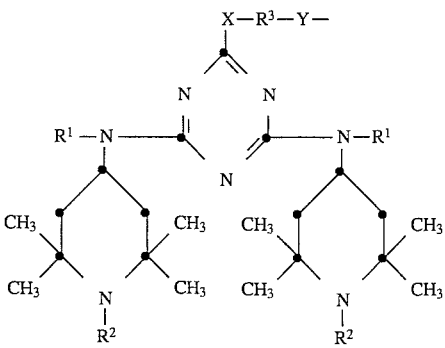

and these also may be the same or different. Again, it is convenient and easy to prepare compounds in which these groups are the same, and so such groups are preferred. The groups represented by $R^4$ may be the same as or different from the groups represented by $R^2$.

Preferred compounds of the present invention include those having the formula (I), wherein:
1. $R^1$ represents a hydrogen atom, a $C_1$–$C_8$ alkyl group, an alkoxyalkyl group having a total of from 3 to carbon atoms, an acetyl group, a benzyl group or a group of formula (II), as shown above, in which $R^4$ represents a hydrogen atom, a $C_1$–$C_4$ alkyl group, an acetyl group or a benzyl group.
2. $R^2$ represents a hydrogen atom, a $C_1$–$C_4$ alkyl group, an acetyl group or a benzyl group.
3. $R^3$ represents a $C_1$–$C_6$ alkylene group or a $C_1$–$C_6$ alkylene group interrupted by at least one oxygen atom.
4. X represents an oxygen atom or a group of formula —NH— or —$NCH_3$—.
5. Y represents a group of formula —OCO—, —CONH— or —COO—.
6. n is 2 and Z represents a $C_1$–$C_{10}$ alkylene group, a $C_1$–$C_{10}$ alkylene group interrupted by at least one oxygen atom, a group of formula (V), as shown above, in which:
   $R^6$ represents a hydrogen atom or a methyl group; and p is 1 or 2,
or a group of formula (VI), as shown above, in which:
   R represents a $C_2$ or $C_3$ alkylene group.
7. n is 3 and Z represents a $C_3$–$C_6$ alkanetriyl group or a group of formula (VII), as shown above, in which:
   $R^7$, $R^8$ and $R^9$ are independently selected from the group consisting of alkylene groups having from 1 to 4 carbon atoms, provided that the total number of carbon atoms in $R^7+R^8+R^9$ is from 3 to 6.

Of the compounds in classes 1–7 above, we prefer those in which $R^1$ is as defined in 1 above, $R^2$ is as defined in 2 above $R^3$ is as defined in 3 above, X is as defined in 4 above, Y is as defined in 5 above, and n and Z are as defined in 6 or 7 above.

Still more preferred compounds are those of formula (I) in which:

8. $R^1$ represents a hydrogen atom, a $C_1$–$C_8$ alkyl group, a benzyl group or a group of formula (II), as shown above, in which R represents a hydrogen atom, a methyl group or a benzyl group.
9. $R^2$ represents a hydrogen atom, a methyl group or a benzyl group.
10. $R^3$ represents a $C_1$–$C_4$ alkylene group or a $C_1$–$C_4$ alkylene group interrupted by at least one oxygen atom.

Of the compounds in classes 8–10 above, we prefer those in which $R^1$ is as defined in 8 above, $R^2$ is as defined in 9 above, $R^3$ is as defined in 10 above, X is as defined in 4 above, Y is as defined in 5 above, and n and Z are as defined in 6 above.

The most preferred compounds of the present invention are those in which:

11. $R^1$ represents a hydrogen atom or a $C_1$–$C_4$ alkyl group.
12. $R^2$ represents a hydrogen atom or a methyl group.
13. $R^3$ represents a $C_1$–$C_2$ alkylene group.
14. X represents a group of formula —NH— or —NCH$_3$—.
15. n is 2 and Z represents a $C_2$–$C_8$ alkylene group or a $C_2$–$C_8$ alkylene group interrupted by at least one oxygen atom.

Of the compounds in classes 11–15 above, we prefer those in which $R^1$ is as defined in 11 above, $R^2$ is as defined in 12 above, $R^3$ is as defined in 13 above, X is as defined in 14 above, Y is as defined in 5 above, and n and Z are as defined in 15 above.

The compounds of the present invention have several basic nitrogen atoms in their molecular structure and can thus form acid addition salts, which are also included within the scope of this invention. There is no particular restriction on the nature of the acid used to form such acid addition salts provided that it does not inhibit stabilization of the high polymer or does not do so to an unacceptable degree. Examples of such acids include: inorganic acids, such as sulfuric acid, hydrochloric acid or phosphoric acid; carboxylic acids such as formic acid, acetic acid, valetic acid, stearic acid, oxalic acid, adipic acid, sebacic acid, maleic acid, benzoic acid, p-t-butylbenzoic acid, 3,5-di-t-butyl-4-hydroxybenzoic acid, salicylic acid or terephthalic acid: sulfonic acids such as methanesulfonic acid or benzenesulfonic acid; and phosphonic acids such as phenylphosphonic acid.

Examples of specific compounds of the invention are those compounds of formula (I) in which $R^1$, $R^2$, X—$R^3$—Y—, n and Z are as defined in the following Table 1. The compounds of the invention are hereinafter, where appropriate, identified by the numbers appended to them in this Table. In the Table, the following abbreviations are used:

| | |
|---|---|
| Ac | acetyl |
| Bu | butyl |
| Bz | benzyl |
| Ddc | dodecyl |
| Et | ethyl |
| Hx | hexyl |
| cHxy | cyclohexan-1,4-diyl |
| Me | methyl |
| Obh | 3,3',5,5'-tetraoxaspirobicyclo-hexan-4,4'-diyl |
| Oc | octyl |
| Odc | octadecyl |
| Ph | phenyl |
| Phy | 1,4-phenylene |
| Pr | propyl |
| Tme | a group of formula: |

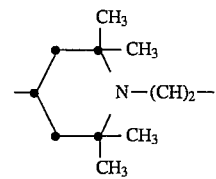

| | |
|---|---|
| Tmp | 2,2,6,6-tetramethyl-4-piperidyl |

TABLE I

| Cpd No | $R^1$ | $R^2$ | X—$R^3$—Y | n | Z |
|---|---|---|---|---|---|
| 1 | H | H | —O(CH$_2$)$_2$OCO— | 2 | —(CH$_2$)$_2$— |
| 2 | H | H | —NH(CH$_2$)$_2$OCO— | 2 | —CH$_2$— |
| 3 | H | H | —NH(CH$_2$)$_2$OCO— | 2 | —(CH$_2$)$_2$— |
| 4 | H | H | —NH(CH$_2$)$_2$OCO— | 2 | —(CH$_2$)$_4$— |
| 5 | H | H | —NH(CH$_2$)$_2$OCO— | 2 | —(CH$_2$)$_8$— |
| 6 | H | H | —NHCH$_2$COO— | 2 | —(CH$_2$)$_2$— |
| 7 | H | H | —NHCH$_2$COO— | 2 | —(CH$_2$)$_4$— |
| 8 | H | H | —NHCH$_2$COO— | 2 | —CH$_2$C(Me)$_2$——ObhC(Me)$_2$CH$_2$— |
| 9 | H | H | —NHCH$_2$CONH— | 2 | —(CH$_2$)$_2$— |
| 10 | H | H | —NH(CH$_2$)$_2$OCONH— | 2 | —(CH$_2$)$_6$— |
| 11 | Me | H | —O(CH$_2$)$_2$OCO— | 2 | —(CH$_2$)$_2$— |
| 12 | Me | H | —O(CH$_2$)$_2$OCO— | 2 | —(CH$_2$)$_4$— |
| 13 | Me | H | —NH(CH$_2$)$_2$OCO— | 2 | —CH$_2$— |
| 14 | Me | H | —NH(CH$_2$)$_2$OCO— | 2 | —(CH$_2$)$_2$— |
| 15 | Me | H | —NH(CH$_2$)$_2$OCO— | 2 | —(CH$_2$)$_4$— |
| 16 | Me | H | —NH(CH$_2$)$_2$OCO— | 2 | —(CH$_2$)$_8$— |
| 17 | Me | Me | —NH(CH$_2$)$_2$OCONH— | 2 | —(CH$_2$)$_6$— |
| 18 | Me | H | —NHCH$_2$COO— | 2 | —(CH$_2$)$_2$— |
| 19 | Me | H | —NHCH$_2$COO— | 2 | —(CH$_2$)$_4$— |
| 20 | Me | H | —NHCH$_2$COO— | 2 | —(CH$_2$)$_2$—O—(CH$_2$)$_2$— |
| 21 | Me | H | —NHCH$_2$CONH— | 2 | —(CH$_2$)$_2$— |
| 22 | Me | H | —NHCH$_2$CONH— | 2 | —(CH$_2$)$_6$— |

TABLE I-continued

| Cpd No | R¹ | R² | X—R³—Y | n | Z |
|---|---|---|---|---|---|
| 23 | Et | H | —O(CH₂)₂OCO— | 2 | —(CH₂)₂— |
| 24 | Et | H | —O(CH₂)₂OCO— | 2 | —(CH₂)₄— |
| 25 | Et | Ac | —O(CH₂)₂OCO— | 2 | -cHxy- |
| 26 | Et | H | —NH(CH₂)₂OCO— | 2 | —CH₂— |
| 27 | Et | H | —NH(CH₂)₂OCO— | 2 | —(CH₂)₂— |
| 28 | Et | H | —NH(CH₂)₂OCO— | 2 | —(CH₂)₄— |
| 29 | Et | H | —NH(CH₂)₂OCO— | 2 | —(CH₂)₈— |
| 30 | Et | H | —NH(CH₂)₂OCO— | 2 | —(CH₂)₁₂— |
| 31 | Et | H | —NH(CH₂)₂OCO— | 2 | —CH₂cHxyCH₂— |
| 32 | Et | Me | —NH(CH₂)₂OCONH— | 2 | —(CH₂)₆— |
| 33 | Et | H | —NHCH₂COO— | 2 | —(CH₂)₂— |
| 34 | Et | H | —NHCH₂COO— | 2 | —(CH₂)₄— |
| 35 | Et | H | —NHCH₂COO— | 2 | —CH₂C(Me)₂Obh-C(Me)₂CH₂— |
| 36 | Et | H | —NHCH₂CONH— | 2 | —(CH₂)₂— |
| 37 | Et | H | —NHCH₂CONH— | 2 | —(CH₂)₄— |
| 38 | Et | H | —NHCH₂CONH— | 2 | —(CH₂)₃Obh(CH₂)₃— |
| 39 | Pr | H | —NH(CH₂)₂OCO— | 2 | —(CH₂)₂— |
| 40 | Pr | Me | —NH(CH₂)₂OCO— | 2 | —(CH₂)₈— |
| 41 | Pr | H | —NHCH₂COO— | 2 | —(CH₂)₄— |
| 42 | Pr | H | —NHCH₂CONH— | 2 | —(CH₂)₃Obh(CH₂)₃— |
| 43 | Pr | Bz | —NHCH₂CONH— | 2 | —(CH₂)₆— |
| 44 | Bu | H | —O(CH₂)₂OCO— | 2 | —(CH₂)₂— |
| 45 | Bu | H | —O(CH₂)₂OCO— | 2 | —(CH₂)₄— |
| 46 | Bu | H | —O(CH₂)₂OCO— | 2 | —(CH₂)₈— |
| 47 | Bu | H | —NH(CH₂)₂OCO— | 2 | —CH₂— |
| 48 | Bu | H | —NH(CH₂)₂OCO— | 2 | —(CH₂)₂— |
| 49 | Bu | H | —NH(CH₂)₂OCO— | 2 | —(CH₂)₄— |
| 50 | Bu | H | —NH(CH₂)₂OCO— | 2 | —(CH₂)₈— |
| 51 | Bu | H | —NH(CH₂)₂OCO— | 2 | —(CH₂)₁₂— |
| 52 | Bu | H | —NH(CH₂)₂OCONH— | 2 | —(CH₂)₂— |
| 53 | Bu | Me | —NH(CH₂)₂OCONH— | 2 | —CH₂PhyCH₂— |
| 54 | Bu | H | —NMe(CH₂)₂OCO— | 2 | —(CH₂)₂— |
| 55 | Bu | H | —NMe(CH₂)₂OCO— | 2 | —(CH₂)₄— |
| 56 | Bu | H | —NMe(CH₂)₂OCO— | 2 | —(CH₂)₈— |
| 57 | Bu | H | —NHCH₂COO— | 2 | —(CH₂)₂— |
| 58 | Bu | H | —NHCH₂COO— | 2 | —(CH₂)₄— |
| 59 | Bu | H | —NHCH₂COO— | 2 | —(CH₂)₂O(CH₂)₂— |
| 60 | Bu | H | —NHCH₂COO— | 2 | —CH₂C(Me)₂Obh-C(Me)₂CH₂— |
| 61 | Bu | Bz | —NHCH₂COO— | 2 | —(CH₂)₂O-Phy-O(CH₂)₂— |
| 62 | Bu | H | —NHCH₂CONH— | 2 | —(CH₂)₆— |
| 63 | Bu | H | —NH(CH₂)₃OCO— | 2 | —(CH₂)₂— |
| 64 | Bu | H | —NH(CH₂)₃OCO— | 2 | —(CH₂)₄— |
| 65 | Hx | H | —NH(CH₂)₂OCO— | 2 | —(CH₂)₄— |
| 66 | Hx | H | —NH(CH₂)₂OCO— | 2 | —(CH₂)₈— |
| 67 | Oc | H | —NH(CH₂)₂OCO— | 2 | —(CH₂)₂— |
| 68 | Oc | H | —NH(CH₂)₂OCO— | 2 | —(CH₂)₄— |
| 69 | Oc | H | —NHCH₂COO— | 2 | —(CH₂)₄— |
| 70 | Oc | H | —NHCH₂CONH— | 2 | —(CH₂)₂— |
| 71 | 2-EtHx | H | —NH(CH₂)₂OCO— | 2 | —(CH₂)₄— |
| 72 | 2-EtHx | H | —NHCH₂COO— | 2 | —(CH₂)₈— |
| 73 | 2-MeOEt | H | —NH(CH₂)₂OCO— | 2 | —(CH₂)₄— |
| 74 | 2-MeOEt | H | —NHCH₂COO— | 2 | —(CH₂)₂— |
| 75 | 3-EtOPr | H | —O(CH₂)₂OCO— | 2 | —CH₂C(Me)₂Obh-C(Me)₂CH₂— |
| 76 | E-EtOPr | H | —O(CH₂)₂OCO— | 2 | —(CH₂)₂O-Phy-O(CH₂)₂— |
| 77 | Ac | Ac | —O(CH₂)₂OCO— | 2 | —(CH₂)₂— |
| 78 | Ac | Ac | —NH(CH₂)₂OCO— | 2 | —(CH₂)₄— |
| 79 | Tmp | H | —NH(CH₂)₂OCO— | 2 | —(CH₂)₂— |
| 80 | Tmp | H | —O(CH₂)₂OCO— | 2 | —(CH₂)₄— |
| 81 | Tmp | H | —NHCH₂COO— | 2 | —(CH₂)₈— |
| 82 | 1-AcTmp | Ac | —O(CH₂)₂OCO— | 2 | —CH₂— |
| 83 | Me | H | —NH(CH₂)₂OCO— | 3 | N(—CH₂—)₃ |
| 84 | Et | H | —O(CH₂)₂OCO— | 3 | N(—CH₂—)₃ |
| 85 | Et | H | —[O(CH₂)₂]₂OCO— | 3 | N(—CH₂—)₃ |
| 86 | Bu | H | —O(CH₂)₂OCO— | 3 | N(—CH₂—)₃ |
| 87 | Et | H | —NH(CH₂)₂OCO— | 3 | N(—CH₂—)₃ |
| 88 | Bu | H | —NH(CH₂)₂OCO— | 3 | N(—CH₂—)₃ |
| 89 | Bu | H | —NMe(CH₂)₂OCO— | 3 | N(—CH₂—)₃ |
| 90 | Me | H | —NH(CH₂)₂OCO— | 3 | —CH₂CHCHCH₃ (with \| \| ) |

TABLE I-continued

| Cpd No | R¹ | R² | X—R³—Y | $\underline{n}$ | Z |
|---|---|---|---|---|---|
| 91 | Et | H | —NH(CH₂)₂OCO— | 3 | —CH₂CHCHCH₃ (with two branches) |
| 92 | Bu | H | —NH(CH₂)₂OCO— | 3 | —CH₂CHCHCH₃ (with two branches) |
| 93 | Et | H | —NHCH₂COO— | 3 | —CH₂C(CH₂—)₂Et |
| 94 | Bu | H | —NHCH₂COO— | 3 | —CH₂C(CH₂—)₂Et |
| 95 | Me | H | —NHCH₂COO— | 3 | —CH₂CHCH₂— (with one branch) |
| 96 | Et | H | —NHCH₂COO— | 3 | —CH₂CHCH₂— (with one branch) |
| 97 | Me | H | —NH(CH₂)₂OCO— | 4 | —CH₂CHCHCH₂— (with two branches) |
| 98 | Et | H | —NH(CH₂)₂OCO— | 4 | —CH₂CHCHCH₂— (with two branches) |
| 99 | Bu | H | —NH(CH₂)₂OCO— | 4 | —CH₂CHCHCH₂— (with two branches) |
| 100 | Me | H | —NHCH₂COO— | 4 | —CH₂C(CH₂—)₂CH₂— |
| 101 | Et | H | —NHCH₂COO— | 4 | —CH₂C(CH₂—)₂CH₂— |
| 102 | Bu | H | —NHCH₂COO— | 4 | —CH₂C(CH₂—)₂CH₂— |
| 103 | Et | H | —NHCH₂COO— | 4 | —CH₂CHOCHCH₂— (with two branches) |
| 104 | Bu | H | —NHCH₂COO— | 4 | —CH₂CHOCHCH₂— (with two branches) |
| 105 | Me | H | —NHCH₂COO— | 2 | —(CH₂)₆— |
| 106 | Me | H | —NHCH₂COO— | 2 | —(CH₂)₈— |
| 107 | Me | H | —NHCH₂COO— | 2 | —[(CH₂)₂—O]₂—(CH₂)₂— |
| 108 | Me | H | —NHCH₂COO— | 2 | —CH₂C(Me)₂Obh—C(Me)₂CH₂— |
| 109 | Me | H | —NHCH(Me)COO— | 2 | —(CH₂)₄— |
| 110 | Me | H | —NHCH(Me)COO— | 2 | —(CH₂)₂—O—(CH₂)₂— |
| 111 | Me | H | —NH(CH₂)₅COO— | 2 | —(CH₂)₄— |
| 112 | Me | H | —NH(CH₂)₅COO— | 2 | —(CH₂)₆— |
| 113 | Et | H | —NHCH₂COO— | 2 | —(CH₂)₆— |
| 114 | Et | H | —NHCH₂COO— | 2 | —(CH₂)₂—O—(CH₂)₂— |
| 115 | Et | H | —NHCH₂COO— | 2 | —[(CH₂)₂—O]₂—(CH₂)₂— |
| 116 | Et | H | —NHCH₂COO— | 2 | —CH₂—C(Me)₂—CH₂— |
| 117 | Et | H | —NHCH₂COO— | 2 | —CH₂—CH(Me)— |
| 118 | Et | H | —NHCH₂COO— | 2 | Tme |
| 119 | Et | H | —NHCH(Me)COO— | 2 | —(CH₂)₂— |
| 120 | Et | H | —NHCH(Me)COO— | 2 | —(CH₂)₄— |
| 121 | Et | H | —NHCH(Me)COO— | 2 | —(CH₂)₆— |
| 122 | Et | H | —NHCH(Me)COO— | 2 | —(CH₂)₂—O—(CH₂)₂— |
| 123 | Et | H | —NHCH(Me)COO— | 2 | —[(CH₂)₂—O]₂—(CH₂)₂— |
| 124 | Et | H | —NHC(Me)₂COO— | 2 | —(CH₂)₄— |
| 125 | Et | H | —NHC(Me)₂COO— | 2 | —(CH₂)₆— |
| 126 | Et | H | —NHC(Me)₂COO— | 2 | —(CH₂)₂—O—(CH₂)₂— |
| 127 | Et | H | —NH(CH₂)₅COO— | 2 | —(CH₂)₄— |
| 128 | Et | H | —NH(CH₂)₅COO— | 2 | —(CH₂)₆— |
| 129 | Et | H | —NH(CH₂)₅COO— | 2 | —(CH₂)₂—O—(CH₂)₂— |
| 130 | Et | H | —NHCH₂CONH— | 2 | —(CH₂)₆— |
| 131 | Et | H | —NHCH(Me)CONH— | 2 | —(CH₂)₂— |
| 132 | Et | H | —NHCH(Me)CONH— | 2 | —(CH₂)₆— |
| 133 | Pr | H | —NHCH₂COO— | 2 | —(CH₂)₆— |
| 134 | Pr | H | —NHCH(Me)COO— | 2 | —(CH₂)₄— |
| 135 | Pr | H | —NHCH(Me)COO— | 2 | —(CH₂)₂—O—(CH₂)₂— |
| 136 | Pr | H | —NH(CH₂)₅COO— | 2 | —(CH₂)₄— |
| 137 | Pr | H | —NH(CH₂)₅COO— | 2 | —(CH₂)₂—O—(CH₂)₂— |
| 138 | Pr | H | —NHCH₂CONH— | 2 | —(CH₂)₂— |
| 139 | Bu | H | —NHCH₂COO— | 2 | —(CH₂)₆— |
| 140 | Bu | H | —NHCH₂COO— | 2 | —[(CH₂)₂—O]₂—(CH₂)₂— |
| 141 | Bu | H | —NHCH₂COO— | 2 | —CH₂—C(Me)₂—CH₂— |
| 142 | Bu | H | —NHCH₂COO— | 2 | —CH₂—CH(Me)— |
| 143 | Bu | H | —NHCH₂COO— | 2 | Tme |
| 144 | Bu | H | —NHCH(Me)COO— | 2 | —(CH₂)₄— |
| 145 | Bu | H | —NHCH(Me)COO— | 2 | —(CH₂)₆— |

TABLE I-continued

| Cpd No | R¹ | R² | X—R³—Y | n | Z |
|---|---|---|---|---|---|
| 146 | Bu | H | —NHCH(Me)COO— | 2 | —(CH₂)₂—O—(CH₂)₂— |
| 147 | Bu | H | —NHCH(Me)COO— | 2 | —[(CH₂)₂—O]₂—(CH₂)₂— |
| 148 | Bu | H | —NH(CH₂)₅COO— | 2 | —(CH₂)₄— |
| 149 | Bu | H | —NH(CH₂)₅COO— | 2 | —(CH₂)₆— |
| 150 | Bu | H | —NHCH(Me)CONH— | 2 | —(CH₂)₄— |
| 151 | Bu | H | —NH(CH₂)₅CONH— | 2 | —(CH₂)₂— |
| 152 | Oc | H | —NHCH(Me)COO— | 2 | —(CH₂)₆— |
| 153 | Ddc | H | —NHCH₂COO— | 2 | —(CH₂)₄— |
| 154 | Odc | H | —NHCH(Me)COO— | 2 | —(CH₂)₆— |
| 155 | Bu | H | —NHCH₂COO— | 2 | —(CH₂)₂CH(Me)— |
| 156 | Et | H | —NHCH₂COO— | 2 | —(CH₂)₂CH(Me)— |
| 157 | Me | H | —NHCH(Me)COO— | 2 | —(CH₂)₆— |
| 158 | Me | H | —NH(CH₂)₂COO— | 2 | —(CH₂)₂—O—(CH₂)₂— |

Of the compounds listed above, the following compounds are preferred, that is to say Compounds No. 23, 27, 29, 33, 34, 46, 49, 50, 57, 58, 59, 62, 64, 85, 86, 105 and 114, and the following are the most preferred:

27. Bis{2-(2,4-bis[N-ethyl-N-(2,2,6,6-tetramethyl-4-piperidyl)amino] -1,3,5-triazin-6-yl)aminoethyl}succinate;
29. Bis{2-(2,4-bis N-ethyl-N-(2,2,6,6-tetramethyl-4-piperidyl)amino] -1,3,5-triazin-6-yl)aminoethyl}sebacate;
33. Ethylene glycol bis{N-(2,4-bis N-ethyl-N-(2,2,6,6-tetramethyl-4-piperidyl)amino] -1,3,5-triazin-6-yl)glycinate};
34. Butane-1,4-diol bis{N-(2,4-bis[N-ethyl-N-(2,2,6,6-tetramethyl-4-piperidyl)amino] -1,3,5-triazin-6-yl )glycinate};
49. Bis{2-(2,4-bis(N-butyl-N-(2,2,6,6-tetramethyl-4-piperidyl)amino]-1,3,5-triazin-6-yl)aminoethyl}adipate;
50. Bis(2-(2,4-bis[N-butyl-N-(2,2,6,6-tetramethyl-4piperidyl)amino] -1,3,5-triazin-6-yl)aminoethyl}sebacate;
105. Hexane-1,6-diol bis{N-(2,4-bis N-methyl-N(2,2,6,6-tetramethyl-4-piperidyl)amino] -1,3,5-triazin-6-yl)glycinate}; and
114. Diethylene glycol bis{N-(2,4-bis[N-ethyl-N-(2,2,6,6-tetramethyl-4-piperidyl)amino] -1,3,5-triazinyl)glycinate};
and acid addition salts thereof.

In general terms, the compounds of the present invention can be prepared by reacting a compound of formula (VIII):

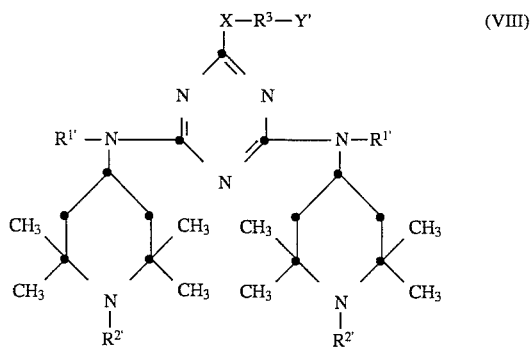

(VIII)

in which:

R¹' represents a hydrogen atom, an alkyl group having from 1 to 18 carbon atoms, an alkoxyalkyl group having from 3 to 22 carbon atoms, a phenylalkyl group in which the alkyl part has from 1 to 4 carbon atoms and in which the phenyl part is unsubstituted or has at least one substituent selected from the group consisting of $C_1$–$C_4$ alkyl groups, $C_1$–$C_4$ alkoxy groups and halogen atoms, or a group of formula (IX):

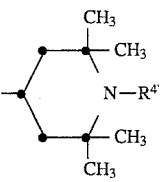

(IX)

wherein R⁴' has the same meanings as defined below for R²';

R²' represents a hydrogen atom an alkyl group having from 1 to 18 carbon atoms or a phenylalkyl group in which the alkyl part has from 1 to 4 carbon atoms and in which the phenyl part is unsubstituted or has at least one substituent selected from the group consisting of $C_1$–$C_4$ alkyl groups. $C_1$–$C_4$ alkoxy groups and halogen atoms;

Y' represents a group of formula —COOR⁷, wherein R⁷ represents a $C_1$–$C_4$ alkyl group, or a hydroxy group: and X and R³ are as defined above:

with a compound of formula (X):

(Y")ₙ–z   (X)

(in which:

when Y' represents a group of formula —COOR⁷, then Y" represents a hydroxy group or an amino group. whereas when Y' represents a hydroxy group then represents a group of formula —COR⁸ wherein R⁸ represents a $C_1$–$C_4$ alkoxy group or a halogen atom.

or an isocyanate group: and

Z and n are as defined above:

and then, if required, converting any atom or group represented by R¹' to a different atom or group represented by R¹ and, if required, converting any atom or group represented by R²' to a different atom or group represented by R², preferably by acylation of a compound in which one or both of R¹' and R²' represents a hydrogen atom to prepare a compound in which one or both of R¹ and R² represents an acyl group;

and, if required, converting the resulting compound to an acid addition salt thereof or converting a salt to the free base.

In more detail, the compounds of the present invention can be prepared by the sequence of reactions shown in Reaction Scheme A:

Reaction Scheme A

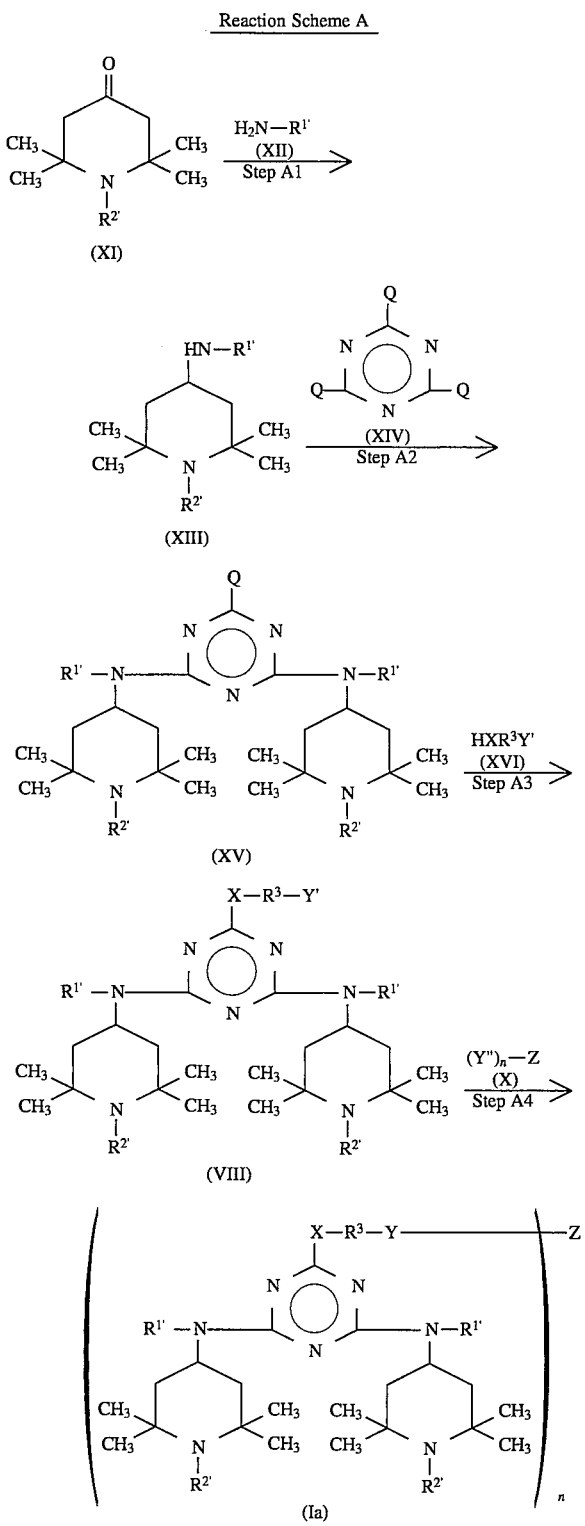

In the formulae shown above, $R^{1'}$, $R^{2'}$, $R^{3'}$, X Y, Y', Y", n and Z are as defined above; and Q represents a halogen atom, such as a chlorine, bromine or iodine atom, preferably a chlorine atom.

In Step A1 of Method A a compound of formula (XIII) is prepared by reacting a compound of formula (XI) with a compound of formula (XII) under catalytic reduction conditions.

There is no particular restriction on the nature of the catalyst to be employed in the reaction, and any catalyst capable of being used in conventional catalytic reduction reactions can equally be used here. Preferred examples of such catalysts include palladium-on-carbon, palladium black, platinum oxide and Raney nickel, of which platinum oxide is particularly preferred.

The reaction is preferably effected in the presence of a solvent, the nature of which is not critical to the reaction, provided that it does not interfere with the reaction. Examples of suitable solvents include water or an alcohol, such as methanol, ethanol or propanol.

The reaction is effected in an atmosphere of hydrogen, and the hydrogen pressure to be used in the reaction is usually at least atmospheric pressure, e.g. from atmospheric pressure to 10 atmospheres. The reaction may be carried out over a wide range of temperatures, and the precise temperature chosen is not particularly critical to the reaction. In general, we prefer that the reaction should be carried out at a temperature in the range of from room temperature to 100° C. The time required for the reaction may vary widely, depending on the nature of the starting materials and the catalyst as well as upon the reaction temperature, but a period of from 30 minutes to 5 hours will usually suffice.

The compound of formula (XII) can be used in the form of a salt, and there is no substantial restriction on the nature of the salt to be employed. Examples of such salts include: salts with mineral acids, such as hydrochloric acid, nitric acid or sulfuric acid: salts with carboxylic acids, such as acetic acid, trifluoroacetic acid, adipic acid or benzoic acid: salts with sulfonic acids, such as methanesulfonic acid or p-toluenesulfonic acid: and salts with phosphonic acids, such as phenylphosphonic acid.

In Step A2 and Step A3 of Method A, compounds of formulae (XV) and (VIII) are prepared, respectively, by reacting the compound of formula (XIII) with the compound of formula (XIV) and by reacting the compound of formula (XV) with the compound of formula (XVI). These reactions are preferably conducted sequentially and take place under essentially the same conditions. If desired, they may be carried out without intermediate isolation of the compound of formula (XV).

A compound of formula (XV) in which each group represented by $R^{1'}$ in the two piperidyl groups and/or each group represented by $R^{2'}$ in those groups is different can be prepared by reacting the compound of formula (XIV) first with about an equimolar amount of a first compound of formula (XIII), and then with about an equimolar amount of another compound of formula (XIII).

The reactions are preferably carried out in the presence of a solvent, the nature of which is not critical, provided that it does not interfere with the reactions. Examples of suitable solvents include: water; ketones, such as acetone or methyl ethyl ketone: ethers, such as diethyl ether, tetrahydrofuran or dioxane; aromatic hydrocarbons, such as benzene, toluene or xylene; saturated hydrocarbons, such as heptane, octane, isooctane, cyclohexane or ethylcyclohexane; and mixtures of any one or more of the above organic solvents with water. We particularly prefer to use a mixture of water and acetone.

The reactions may be carried out over a wide range of temperatures, and the precise temperature chosen is not particularly critical to the reactions. In general, we prefer that the reactions should be carried out at a temperature in the range of from 0° to 200° C., more preferably from room temperature to 150° C. The time required for the reactions may vary widely, depending on the nature of the starting materials as well as upon the reaction temperature, but a period of from 30 minutes to 30 hours will usually suffice for each of the reactions.

The reactions are preferably effected in the presence of an acid binding agent. Any compound capable of binding to the hydrohalic acid HQ produced in the reaction and effectively removing the acid from participation in the reaction may be employed, provided that it does not otherwise interfere with the reaction. Examples of such acid binding agents include: inorganic bases, especially alkali metal hydroxides and carbonates, such as sodium hydroxide, potassium hydroxide, sodium carbonate or potassium carbonate; and organic bases, such as triethylamine, pyridine, N,N-dimethylaniline or 1,8-diazabicyclo[4.3.0]undeca-7-ene (DBU). Of these, we prefer sodium hydroxide, potassium hydroxide, sodium carbonate or potassium carbonate.

In Step A4 of Method A, a compound of formula (Ia) is prepared by reacting a compound of formula (VIII) with a compound of formula (X) in a suitable ratio in an inert solvent. In the compounds of formulae (VIII) and (X), when Y' represents a hydroxy group and Y" represents a group of formula —$COR^8$ (wherein $R^8$ represents a lower alkoxy group), or when Y' represents a group of formula —$COOR^7$ (wherein $R^7$ represents a lower alkyl group) and Y" represents a hydroxy group or an amino group, the reaction is preferably conducted in an inert solvent and in the presence of a base. Although the reaction temperature is not critical and the reaction will take place over a wide range of temperatures, we normally prefer to carry out the reaction at an elevated temperature, usually at a reaction temperature of from 80° to 150° C. The time required for the reaction may vary widely, depending on the nature of the starting materials as well as upon the reaction temperature, but a period of from 30 minutes to 5 hours will usually suffice. In general, we prefer that the reaction should be carried out whilst distilling off the lower alcohol formed in the course of the reaction.

A compound of formula (Ia) in which each group of formula:

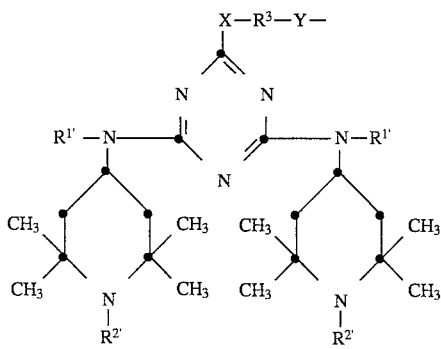

is different can be prepared by reacting the compound of formula (X) stepwise first with about an equimolar amount of a first compound of formula (VIII), then with about an equimolar amount of a second compound of formula (VIII), and so on.

There is no particular restriction on the nature of the base to be employed, provided that it has no adverse effect on the reaction or on the reagents. Examples of suitable bases include: alkali metal compounds, especially alkoxides, hydroxides and amides, such as sodium methoxide, sodium ethoxide, potassium t-butoxide, sodium hydroxide, potassium hydroxide or lithium amide: and titanate compounds, such as tetraisopropyl or tetrabutyl titanate. Of these, we prefer sodium ethoxide, potassium hydroxide and the titanate compounds. The nature of the solvent employed is not critical, provided that it does not interfere with the reaction. Examples of suitable solvents include: hydrocarbons, which may be aliphatic, aromatic or alicyclic, such as benzene, toluene, xylene, heptane, octane, isooctane, cyclohexane or ethylcyclohexane.

When Y' represents a hydroxy group and Y" represents a group of formula —$COR^8$ (wherein $R^8$ represents a halogen atom), the reaction is preferably conducted in an inert solvent and in the presence or absence of an acid binding agent. Although the reaction temperature is not critical and the reaction will take place over a wide range of temperatures, we normally prefer to carry out the reaction at room temperature or at an elevated temperature, usually at a reaction temperature of from room temperature to 130° C. The time required for the reaction may vary widely, depending on the nature of the starting materials as well as upon the reaction temperature, but a period of from 30 minutes to 3 hours will usually suffice. The reaction is preferably effected in the presence of an acid binding agent. Any compound capable of binding to the hydrohalic acid produced in the reaction and effectively removing the acid from participation in the reaction may be employed, provided that it does not otherwise interfere with the reaction. Examples of such acid binding agents include those exemplified in relation to Steps A2 and A3 of Method A.

The nature of the solvent employed is not critical, provided that it does not interfere with the reaction. Examples of suitable solvents include: aromatic hydrocarbons, such as benzene, toluene or xylene; halogenated aliphatic hydrocarbons, such as chloroform or trichloroethane; and ethers, such as diethyl ether, tetrahydrofuran or dioxane.

When Y' represents a hydroxy group and Y" represents an isocyanate group, the reaction is preferably conducted in an inert solvent. There is no particular restriction on the nature of the solvent to be employed, provided that it has no adverse effect on the reaction or on the reagents involved. Examples of suitable solvents include: aromatic hydrocarbons, such as benzene, toluene or xylene: and aliphatic and alicyclic hydrocarbons, such as heptane, octane, isooctane, cyclohexane and ethylcyclohexane. The reaction can take place over a wide range of temperatures, and the precise reaction temperature is not critical to the invention. In general, we find it convenient to carry out the reaction an a temperature from room temperature to 160° C. The time required for the reaction may also vary widely, depending on many factors, notably the reaction temperature and the nature of the reagents. However, provided that the reaction is effected under the preferred conditions outlined above, a period of from 30 minutes to 5 hours will usually suffice.

Compounds of formula (I) wherein either one or both of $R^1$ and $R^2$ represents an acyl group can be obtained by subjecting the compound of formula (Ia) wherein either one or both of $R^{1'}$ and $R^{2'}$ represents a hydrogen atom to an acylation reaction as an additional step.

The acylation reaction can be conducted in the same manner as described above in Step A4 of Method A, using an active derivative of a corresponding carboxylic acid (e.g. an acid halide, acid anhydride or lower alkyl ester) as the acylating agent.

After completion of the reaction, the desired product in each step can be collected from the reaction mixture by conventional means. For example, the desired product can be obtained by the following procedures: when insolubles are present in the reaction mixture, filtering off such insolubles: or, when the reaction mixture is acidic or basic, neutralizing the reaction mixture: adding water thereto; extracting the resulting mixture with a water-immiscible organic solvent: drying the extract thus obtained: and then distilling the solvent from the extract. The desired compound thus obtained may be further purified, if necessary, by means of a such conventional means as the various chromatography techniques, e.g. column chromatography or preparative thin layer chromatography, or other means, such as distillation or recrystallization.

An alternative method of preparing the compound of formula (VIII), which may then be used to prepare the compounds of the present invention, is illustrated in Reaction Scheme B:

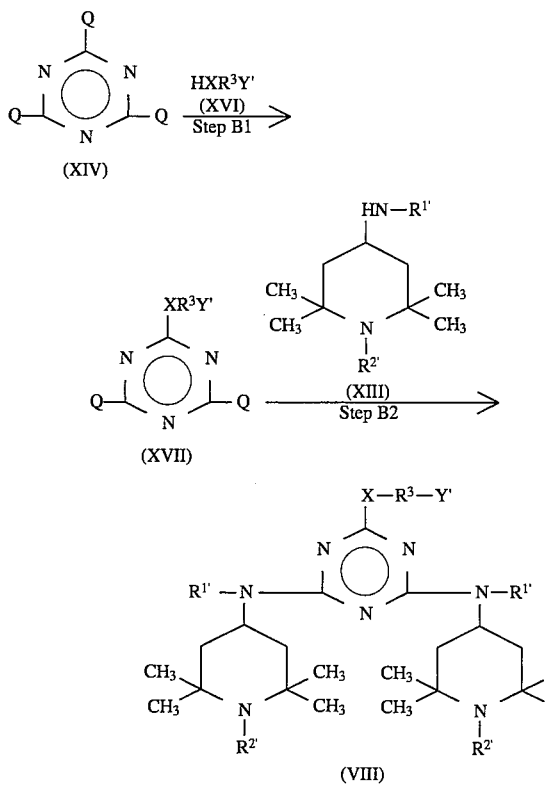

In the above formulae, Q, X, Y', $R^{1'}$, $R^{2'}$ and $R^3$ are as defined above.

In Step B1, the compound of formula (XVII) is prepared by reacting the compound of formula (XIV) with the compound of formula (XVI). In Step B2 the compound of formula (VIII) is prepared by reacting the compound of formula (XVII) with the compound of formula (XIII). These steps are equivalent to Steps A2 and A3 of Reaction Scheme A, and may be effected using the same reaction conditions.

The piperidyl-triazine derivatives and acid addition salts thereof of the present invention have excellent compatibility with polymers, less volatility or blooming liability than many conventional polymer stabilizers, as well as excellent light and heat stabilizing ability. Accordingly they can be employed for stabilizing a wide variety of synthetic high polymer compounds.

Examples of synthetic high polymer compounds which can be stabilized by the compounds of the present invention include:

Olefin and Diene Polymers

Homopolymers of olefins or dienes, for example, polyethylene (which can be low density, linear-chain low density, high density or crosslinked), polypropylene, polyisobutylene, polybutene-1, polymethylbutene-1, polymethylpentene-1, polyisoprene or polybutadiene. Mixtures of two or more of the homopolymers mentioned above, for example, mixtures of polypropylene with polyethylene, with polybutene-1 or with polyisobutylene. Copolymers of olefins with other olefins and/or with dienes, for example, ethylene/propylene copolymers, propylene/butene-1 copolymers, propylene/isobutene copolymers, ethylene/butene-1 copolymers, and also terpolymers of ethylene with propylene and a diene (e.g. hexadiene, dicyclopentadiene or ethylidenenorbornene).

Styrene polymers

Polystyrene, and copolymers of styrene or α-methylstyrene with other ethylenically unsaturated compounds, for example, styrene-maleic anhydride copolymer, styrene-butadiene copolymer, styrene-acrylonitrile copolymer, styrene-acrylonitrile-methyl methacrylate copolymer, styrene-acrylonitrile-acrylate copolymers, styrene-acrylonitrile copolymer modified with an acrylate polymer in order to give a high impact strength or styrene polymer modified with an EPDM (ethylene-propylene-diene polymer) in order to give a high impact strength. Graft copolymers of styrene, for example, styrene on polybutadiene, styrene and acrylonitrile on polybutadiene and mixtures thereof with the above copolymers, such as those known as acrylonitrile-butadiene-styrene or ABS polymers.

Halogen-containing polymers

Especially vinyl and vinylidene polymers, such as polyvinyl chloride, polyvinylidene chloride, polyvinyl fluoride, polychloroprene, chlorinated rubbers, chlorinated vinyl-vinylidene chloride copolymer, chlorinated polyethylene, vinyl chloride-vinylidene chloride copolymer, vinyl chloride-ethylene copolymer, vinyl chloride-vinyl acetate copolymer and vinylidene chloride-vinyl acetate copolymer.

Polymers which are derived from α,β-unsaturated acids and their derivatives

Polyacrylates, polymethacrylates, polyacrylamides and polyacrylonitrile.

Polymers which are derived from unsaturated alcohols and amines or their acyl derivatives or acetals Polyvinyl alcohol, polyvinyl acetate, polyvinyl stearate, polyvinyl benzoate, polyvinyl maleate, polyvinyl butyral, polyallyl phthalate, polyallyl melamine and copolymers of the monomers forming these polymers with other vinyl compounds, such as ethylene-vinyl acetate copolymers.

Epoxy polymers

Homopolymers and copolymers of epoxides, such as polyethylene oxide and their copolymers with bis-glycidyl ethers.

Polyacetals, polyalkylene oxides and polyphenylene oxides

Polyoxymethylene, oxymethylene-ethylene oxide copolymer, polyoxyethylene, polypropylene oxide, polyisobutylene oxide and polyphenylene oxide.

Polyurethanes and polyureas

Polycarbonates

Polysulfones

Polyamides and copolyamides

Polyamides and copolyamides which are derived from diamines and aliphatic or aromatic dicarboxylic acids and/or from aminocarboxylic acids or the corresponding lactams, such as Nylon 6, Nylon 6/6, Nylon 6/10, Nylon 11 and Nylon 12.

Polyesters

Polyesters which are derived from dicarboxylic acids and dialcobols and/or from hydroxycarboxylic acids or the corresponding lackones, such as polyethylene terephthalate, polybutylene terephthalate and polycyclohexane-1,4-dimethyleneterephthalate.

Crosslinked polymers

Crosslinked polymers which are derived from (a) an aldehyde and from (b) a phenol, urea or melamine, such as phenol-formaldehyde resins, urea-formaldehyde resins and melamine-formaldehyde resins, and diallylphthalate resins.

Alkyd resins

Glycerol/phthalic acid resins and their mixtures with melamine-formaldehyde resins.

Unsaturated polyester resins

Derived from copolymers of saturated and unsaturated dicarboxylic acids with polyhydric alcohols and a vinyl compound as the crosslinking agent and also halogenated products thereof modified to have flame retardancy.

The amount of the compound of the invention employed as a stabilizer will depend upon various factors, for example the nature and properties of the polymer, the intended use of the polymer composition and whether or not there are any other stabilizers present. In general, however, the stabilizers of the present invention will be added to the polymers in an amount of from 0.01 to 5% by weight, based on the weight of the polymer. However, the most effective amount of stabilizer depends upon the nature of the polymer and specifically:

For olefin, diene and styrene polymers, we prefer to use from 0.01 to 2.0% by weight of stabilizer, based on the polymer, more preferably from 0.02 to 1.0% by weight.

For polymers derived from vinyl chloride or vinylidene chloride, we prefer to use from 0.01 to 1.0% by weight of stabilizer, based on the weight of the polymer, more preferably from 0.02 to 0.5% by weight.

For polyurethanes and polyamides, we prefer to use from 0.01 to 5.0% by weight of stabilizer, based on the weight of polymer, more preferably from 0.02 to 2.0% by weight.

If desired, two or more of the compounds of the invention may be used together as stabilizers and, if desired, other stabilizers may be used in combination with one or more of the stabilizers of the invention.

The stabilizers of the invention can easily be mixed, employing conventional techniques, into the polymer or prepolymer at any suitable stage prior to preparation of shaped articles or other products from the polymer compositions. For example, the stabilizers may be mixed into the polymer in the molten condition or as dry pulverized materials or a suspension or emulsion of the stabilizer or stabilizers may be mixed with a solution, suspension or emulsion of the polymer.

It is possible to incorporate other additives commonly employed in polymer technology into the stabilized polymer compositions of the invention. Examples of such additives include:

Phenolic antioxidants:

2,6-di-t-butyl-N-cresol=stearyl 3-(4-hydroxy3,5-di-t-butylphenyl)propionate: distearyl (4-hydroxy-3-methyl-5-t-butylbenzyl)malonate; 2,2'-methylenebis(4-methyl-6-t-butylphenol): 4,4'-methylenebis(2,6-di-t-butylphenol). 2,2'-methylenebis[6-(1-methylcyclohexyl)-D-cresol]; bis[3,3-bis(4-hydroxy-3-t-butylphenyl)butyric acid]glycol ester: 4,4'-butylidenebis(6-t-butyl-m-cresol); 1,1,3-tris(2-methyl-4-hydroxy-5-t-butylphenyl)butane; 1,3,5-tris(3,5-di-t-butyl-4-hydroxybenzyl)-2,4,6-trimethylbenzene; 3,9-bis[1,1dimethyl-2-3,5-di-t-butyl-4-hydroxyphenyl)ethyl]-2,4,8,10-tetraoxaspiro[ 5.5] undecane: tetrakis[ methylene-3-(3,5-di-t-butyl-4-hydroxyphenyl)propionate] methane-1,3,5-tri(3,5-di-t-butyl-4-hydroxybenzyl)isocyanurate and 1,3,5-tris[3, 5di-t-butyl-4-hydroxyphenyl) propionyloxyethyl] isocyanurate; bis[3-(3,5-di-t-butyl-4-hydroxyphenyl)propionyl]oxamide.

Phosphite series stabilizers:

tris(2,4-di-t-butylphenyl) phosphite, triphenyl phosphite; tris(nonylphenyl) pnosphite: distearylpentaerythritol diphosphite; 4,4-butylidenebis(3-methyl-6-t-butylphenyl-di-tridecyl) phosphite; bis(2,4-di-t-butylphenyl)pentaerythritol diphosphite.

Ultraviolet absorbers:

2-hydroxy-4-methoxybenzophenone; 2-hydroxy-4-octoxybenzopnenone; 2,4-dihydroxybenzophenone; 2-(2'-hydroxy-3'-t-butyl-5'-methylphenyl)-5-chlorobenzotriazole; 2-(2'-hydroxy-3',5'-di-t-butyl-phenyl)-5-chlorobenzotriazole; 2-(2'-hydroxy-5'-methylphenyl)benzotriazole; 2-(2'-hydroxy-3',5'-di-t-amylphenyl) benzotriazole; phenyl salicylate; 2,4-di-t-butylphenyl-3,5-di-t-butyl-4-hydroxybenzoate.

Nickel series stabilizers:

Ni-monoethyl-3,5-di-t-butyl-4-hydroxybenzylphospnonate; butylamine-Ni-2,2'-thiobis(4-t-octylphenolate) complex; Ni-dibutyl-dithiocarbamate; Ni-3,5-di-t-butyl-4-hydroxybenzoate, Metal salts of higher fatty acids:

calcium, magnesium, barium, zinc, cadmium, lead or nickel stearate, and calcium, magnesium, cadmium, barium or zinc laurate.

In addition to the above additives, heavy metal deactivators, nucleating agents, organic tin compounds, plasticizers, epoxy compounds, pigments, fillers, foaming agents, antistatic agents, lubricants, processing aids, etc. can also be used.

Polymers stabilized in this way can be employed in very many different forms, for example as films, fibers, tapes, compression-molding compositions, coating compositions or paints.

The invention is further illustrated by the following Preparations and Examples, wherein all parts and percentages are by weight, unless otherwise specified.

EXAMPLE 1

Bis{2-(2,4-bis[N-ethyl-N-(2,2,6,6-tetramethyl-4-piperidyl)amino]
-1,3,5-triazin-6-yl)oxyethyl}succinate (Compound No. 23)

1.60 g of 2,4-bis-[N-ethyl-N-(2,2,6,6-tetramethyl-4-piperidyl)amino] -6-(2-hydroxyethoxy)-1,3,5-triazine [prepared as described in Preparation 3(B)] and 0.22 g of dimethyl succinate were dissolved in 20 ml of toluene, and a catalytic amount of tetraisopropyl titanate was added to the resulting solution. The resulting mixture was first agitated at 100° to 105° C. for 3 hours whilst the methanol generated was removed by distillation, and then the temperature was elevated to 130° C. to remove the toluene. When this removal was complete, a mixture of ethyl acetate and water was added to the residue, and then the mixture was shaken. The ethyl acetate layer was then separated, dried and concentrated by evaporation under reduced pressure, and the resulting residue was purified by silica gel column chromatography (using a 10:3:1 by volume mixture of diethyl ether, ethanol and triethylamine as eluent), to obtain 920 mg of the title compound as crystals melting at 85° C.

EXAMPLES 2–49

The procedure described in Example 1 was repeated but replacing the 2,4-bis-[N-ethyl-N-(2,2,6,6-tetramethyl-4-piperidyl)amino] -6-(2-hydroxyethylamino)-1,3,5-triazine and dimethyl succinate by other appropriate starting materials, to obtain the following compounds:

Example 2

Bis[2-(2,4-bis(N-ethyl-N-(2,2,6,6-tetramethyl-4-piperidyl)amino)-1,3,5-triazin-6-yl)aminoethyl] adipate (Compound No. 28), melting at 90° C.

Example 3

Bis{2-(2,4-bis[N-ethyl-N-(2,2,6,6-tetramethyl-4-piperidyl)amino]-1,3,5-triazin-6-yl)aminoethyl}sebacate (Compound No. 29), melting at 80° C.

Example 4

Bis{2-(2,4-bis[M-ethyl-N-(2,2,6,6-tetramethyl-4-piperidyl)amino] -1,3,5-triazin-6-yl)aminoethyl} succinate (Compound No. 27), melting at 90° C.

Example 5

Tris<2-{2-(2,4-bis N-ethyl-N-(2,2,6,6-tetramethyl-4piperidyl)amino] -1,3,5-triazin-6-yl)oxyethyl}oxyethyl>nitrilotriacetate (Compound No. 85), melting at 70° to 75° C.

Example 6

Bis{2-(2,4-bis N-butyl-N-(2,2,6,6-tetramethyl-4-piperidyl)amino] -1,3,5-triazin-6-yl)oxyethyl} adipate (Compound No. 45), melting at 55° to 60° C.

Example 7

Bis{2-(2,4-bis N-butyl-N-(2,2,6,6-tetramethyl-4-piperidyl)amino] -1,3,5-triazin-6-yl)oxyethyl]sebacate (Compound No. 46), melting at 45° C.

Example 8

Bis {2-(2,4-bis[N-butyl-N-(2,2,6,6-tetramethyl-4-piperidyl)amino] -1,3,5-triazin-6-yl) oxyethyl]succinate (Compound No. 44), melting at 60° C.

Example 9

Bis<2-{N-methyl-M-(2,4-bis N-butyl-N-(2,2,6,6-tetramethyl-4-piperidyl)amino] -1,3,5-triazin-6-yl)amino}ethyl>sebacate (Compound No. 56), melting at 60° C.

Example 10

Bis<2-{N-methyl-N-(2,4-bis[M-butyl-N-(2,2,6,6-tetramethyl-4-piperidyl)amino] -1,3,5-triazin-6-yl)amino}ethyl>succinate (Compound No. 54), melting at 75° to 80° C.

Example 11

Bis<2-{N-methyl-N-(2,4-bis N-butyl-N-(2,2,6,6-tetramethyl-4-piperidyl)amino] -1,3,5-triazin-6-yl)amino}ethyl>adipate (Compound No. 55), melting at 60° to 70° C.

Example 12

Bis{3-(2,4-bis[N-butyl-N-(2,2,6,6-tetramethyl-4-piperidyl)amino] -1,3,5-triazin-6-yl) aminopropyl} adipate (Compound No. 64 ), melting at 65° to 75° C.

Example 13

Tris<2-{N-methyl-N-(2,4-bis N-butyl-N-(2,2,6,6-tetramethyl-4-piperidyl)amino] -1,3,5-triazin-6-yl)amino]ethyl} nitrilotriacetate (Compound No. 89), melting at 95° to 105° C.

Example 14

Tris{2-(2,4-bis N-butyl-N-(2,2,6,6-tetramethyl-4piperidyl)amino] -1,3,5-triazin-6-yl)oxyethyl}nitrilotriacetate (Compound No. 86), melting at 75° to 80° C.

Example 15

Butane-1,4-diol bis{N-(2,4-bis[N-butyl-N-(2,2,6,6-tetramethyl-4-piperidyl)amino] -1,3,5-triazin-6-yl)glycinate} (Compound No. 58), melting at 75° C.

Example 16

Diethylene glycol bis{N-(2,4-bis N-butyl-N-(2,2,6,6-tetramenhyl-4-piperidyl)amino] -1,3,5-triazin-6-yl)glycinate} (Compound No. 59), melting at 75° C.

Example 17

N,N'-bis{N-(2,4-bis[N-butyl-N-(2,2,6,6-tetramethyl-4-piperidyl)amino] -1,3,5-triazin-6-yl) glycyl}hexamethylenediamine (Compound No. 62), melting at 100° C.

Example 18

Bis{2-(2,4-bis N-methyl-N-(2,2,6,6-tetramethyl-4-piperidyl)amino] -1,3,5- triazin-6-yl)aminoethyl} sebacate (Compound No. 16), melting at 90° C.

Example 19

Bis{2-(2,4-bis[N-butyl-N-(2,2,6,6-tetramethyl-4-piperidyl)amino] -1,3,5-triazin-6-yl)aminoethyl} sebacate (Compound No. 50), melting at 65° C.

Example 20

Bis {2-(2,4-his [N-methyl-N-(2,2,6,6-tetramethyl-4-piperidyl)amino] -1,3,5-triazin-6-yl)aminoethyl} succinate (Compound No. 14), melting at 110° C.

Example 21

Bis{2-(2,4-bis[N-butyl-N-(2,2,6,6-tetramethyl-4-piperidyl)amino] -1,3,5-triazin-6-yl)aminoethyl} succinate (Compound No. 48), melting at 80° C.

Example 22

Bis{2-(2,4-bis[N-methyl-N-(2,2,6,6-tetramethyl-4-piperidyl)amino] -1,3,5-triazin-6-yl)aminoethyl} adipate (Compound No. 15), melting at 100° C.

Example 23

Bis{2-(2,4-bis(N-butyl-N-(2,2,6,6-tetramethyl-4-piperidyl)amino] -1,3,5-triazin-6-yl)aminoethyl} adipate (Compound No. 49), melting at 65° C.

Example 24

N,N'-bis{N-(2,4-bis[N-methyl-N-(2,2,6,6-tetramethyl-4-piperidyl)amino] -1,3,5-triazin-6-yl)glycyl} ethylenediamine (Compound No. 18), melting at 230° C.

Example 25

N,N'-bis{N-(2,4-bis[N-ethyl-N-(2,2,6,6-tetramethyl-4-piperidyl)amino] -1,3,5-triazin-6-yl)glycyl}ethylenediamine (Compound No. 36), melting at 160° C.

Example 26

N,N'-bis{N-(2,4-bis N-methyl-N-(2,2,6,6-tetramethyl-4-piperidyl)amino] -1,3,5-triazin-6-yl)glycyl}hexamethylenediamine (Compound No. 22), melting at 140° C.

Example 27

N,N'-bis{N-(2,4-bis[N-ethyl-N-(2,2,6,6-tetramethyl-4-piperidyl)amino] -1,3,5-triazin-6-yl)glycyl}hexamethylenediamine (Compound No. 130), melting at 135° C.

Example 28

Butane-1,4-diol bis{N-(2,4-bis N-methyl-N-(2,2,6,6-tetramethyl-4-piperidyl)amino] -1,3,5-triazin-6-yl)glycinate} (Compound No. 19), melting at 238° to 241° C.

Example 29

Butane-1,4-diol bis{N-(2,4-bis[N-ethyl-N-(2,2,6,6-tetrametnyl-4-piperidyl)amino] -1,3,5-triazin-6-yl)glycinate} (Compound No. 34), melting at 194° to 196° C.

Example 30

Octane-1,8-diol bis{N-(2,4-bis[N-methyl-N-(2,2,6,6-tetramethyl-4-piperidyl)amino] -1,3,5-triazin-6-yl)glycinate} (Compound No. 106), melting at 100° C.

Example 31

Diethylene glycol bis{N-(2,4-bis N-ethyl-N-(2,2,6,6-tetramethyl-4-piperidyl)amino] -1,3,5-triazin-6-yl)glycinate} (Compound No. 114), melting at 113° C.

Example 32

Diethylene glycol bis{N-(2,4-bis N-methyl-N-(2,2,6,6-tetramethyl-4-piperidyl)amino] -1,3,5-triazin-6-yl)glycinate} (Compound No. 20), melting at 192° to 195° C.

Example 33

Hexane-1,6-diol bis{N-(2,4-bis[M-methyl-N-(2,2,6,6-tetramethyl-4-piperidyl)amino] -1,3,5-triazin-6-yl)glycinate} (Compound No. 105), melting at 175° to 177° C.

Example 34

Hexane-1,6-diol bis{N-(2,4-bis N-ethyl-N-(2,2,6,6-tetramethyl-4-piperidyl)amino] -1,3,5-triazin-6-yl)glycinate} (Compound No. 113), melting at 87° C.

Example 35

Hexane-1,6-diol bis{N-(2,4-bis N-butyl-N-(2,2,6,6-tetramethyl-4-piperidyl)amino] -1,3,5-triazin-6-yl)glycinate} (Compound No. 139), melting at 75° C.

Example 36

2,2-Dimethylpropane-1,3-diol bis{N-(2,4-bis[ N-butyl-N-(2,2,6,6-tetramethyl -4-piperidyl)amino]-1,3,5-triazin-6-yl)glycinate} (Compound No. 141), melting at 75° C.

Example 37

2,2-Dimethylpropane-1,3-diol bis{N-(2,4-bis N-ethyl-N-(2,2,6,6-tetramethyl-4-piperidyl) amino)-1,3,5-triazin-6-yl)glycinate} (Compound No. 116), melting at 80° C.

Example 38

Butane-1,3-diol bis N-(2,4-bis N-butyl-N-(2,2,6,6-tetramethyl-4-piperidyl)amino] -1,3,5-triazin-6-yl)glycinate} (Compound No. 155), melting at 85° C.

Example 39

Butane-1,3-diol bis{N-(2,4-bis(N-ethyl-N-(2,2,6,6-tetramethyl-4-piperidyl) amino)-1,3,5-triazin-6-yl)glycinate} (Compound No. 156), melting at 100° C.

Example 40

Ethylene glycol bis{N-(2,4-bis N-ethyl-N-(2,2,6,6-tetramenhyl-4-piperidyl)amino] -1,3,5-triazin-6-yl)glycinate} (Compound No. 33), melting at 122° to 125° C.

Example 41

Ethylene glycol bis{N-(2,4-bis(N-butyl-N-(2,2,6,6-tetrametnyl-4-piperidyl)amino] -1,3,5-triazin-6-yl)glycinate} (Compound No. 57), melting at 90° C.

Example 42

Triethylene glycol bis{N-(2,4-bis N-methyl-N-(2,2,6,6-tetramethyl-4-piperidyl)amino] -1,3,5-triazin-6-yl)-glycinate} (Compound No. 107), melting at 232° C.

Example 43

Hexane-1,6-diol bis{N-(2,4-bis N-methyl-N-(2,2,6,6-tetramethyl-4-piperidyl)amino] -1,3.5-triazin-6-yl)alanate} (Compound No. 157), melting at 218° to 224° C.

Example 44

Diethylene glycol bis[2-methyl-2-(2,4-bis-[N-ethyl-N-(2,2,6,6-tetramethyl-4-piperidyl)amino] -1,3,5-triazin-6-ylamino)propionate] (Compound No. 126), melting at 90° C.

Example 45

1-<2-{N-(2,4-bis-[N-ethyl-N-(2,2,6,6-tetramethyl-4-piperidyl)amino] -1,3,5-triazin-6-yl)glycyloxy}ethyl>-4-{N-(2,4-bis[N-ethyl-N-(2,2,6,6-tetramethyl-4-piperidyl) amino] -1,3,5-triazin-6-yl)glycyloxy)-2,2,6,6-tetramethylpiperidine (Compund No. 118), melting at 135° to 145° C.

Example 46

3,9-Bis<1,1-dimethyl-2-{N-(2,4-bis N-methyl-N-(2,2,6,6-tetramethyl-4-piperidyl)amino] -1,3,5-triazin-6-yl)glycyl}oxyethyl>-2,4,8,10-tetraoxaspiro[5,5]undecane (Compound No. 108), melting at 130° C.

Example 47

3,9-Bis<1,1-dimethyl-2-{N-(2,4-bis N-ethyl-N-(2,2,6,6-tetramethyl-4-piperidyl)amino] -1,3,5-triazin-6-yl)glycyl}oxyethyl>-2,4,8,10-tetraoxaspiro[5.5]undecane (Compound No. 35), melting at 120° C.

Example 48

Hexane-1,6-diol bis<2-methyl-2-{2,4-bis[N-ethyl-N(2,2,6,6-tetramethyl-4-piperidyl)amino] -1,3,5-triazin-6-ylamino}propionate>(Compound No. 125), melting at 264° to 265° C.

Example 49

Butane-1,4-diol bis<6-N-{2,4-bis N-butyl-N-(2,2,6,6-tetramethyl-4-piperidyl)amino] -1,3,5-triazin-6-yl-amino}hexanoate> (Compound No. 148), melting at 58° C.

PREPARATION 1

1(A) 2,2,6,6-Tetramethyl-4-butylaminopiperidine 155 g of 2,2,6,6-tetramethyl-4-piperidone and 80.0 g of butylamine were dissolved in 300 ml of methanol, and then 2.0 g of platinum oxide were added to the resulting solution, after which the solution was shaken under a pressure of 3 atmospheres of hydrogen in a medium-pressure hydrogenation apparatus at room temperature for 5 hours. At the end of this time, the platinum catalyst was filtered off, and the solvent was removed from the filtrate by distillation under reduced pressure, after which the residue was further purified by distillation under reduced pressure, to yield 201.5 g of the title compound as an oil boiling at 100° to 101° C./5 mmHg (667 Pa).

Preparations 1(B)+1(C)

A procedure similar to that described in Preparation 1(A) was repeated, except that the corresponding piperidone and amino compounds were employed in place of 2,2,6,6-tetramethyl-4-piperidone and butylamine.

1(B) 2,2,6,6-Tetramethyl-4-ethylaminopiperidine, boiling at 80° to 83° C./5 mmHg (667 Pa);

1(C) 2,2,6,6-Tetramethyl-4-methylaminopiperidine, boiling at 68 to 70° C./3.5 mmHg (467 Pa).

PREPARATION 2

2(A) 2-Chloro-4,6-bis[N-(2,2,6,6-tetramethyl-4-piperidyl)butylamino]-1,3,5-triazine A solution of 43.6 g of 2,2,6,6-tetramethyl-4-butylaminopiperidine dissolved in 100 ml of dioxane was added dropwise to a solution of 18.4 g of cyanuric chloride dissolved in 200 ml of dioxane, whilst stirring at 20° to 25° C. The resulting mixture was thereafter stirred at the same temperature for 2 hours, and then for a further 2 hours at 60° to 70° C. At the end of this time, the dioxane was distilled off under reduced pressure. The residue was mixed with a 10 % w/v aqueous solution of potassium carbonate and extracted with ethyl acetate. The extract was dried over potassium carbonate, and then the ethyl acetate was removed by distillation under reduced pressure, to obtain an oil. This oil was purified by silica gel column chromatography (using a 20:1:1 by volume mixture of ethyl acetate, ethanol and triethylamine as eluent) to yield 52.5 g of the title compound melting at 40° to 42° C.

Preparations 2(B)+2(C)

A procedure similar to that described in Preparation 2(A) was repeated, except that the corresponding piperidine derivative was employed in place of 2,2,6,6-tetramethyl-4-butylaminopiperidine, to give the following compounds:

2(B) 2-Chloro-4,6-bis N-(2,2,6,6-tetramethyl-4-piperidyl)ethylamino]-1,3,5-triazine, melting at 126° to 127° C.

2(C) 2-Chloro-4,6-bis N-(2,2,6,6-tetramethyl-4-piperidyl)methylamino]-1,3,5-triazine, melting at 179° to 188° C.

PREPARATION 3

3(A)
2,4,Bis[N-ethyl-N-(2,2,6,6-tetramethyl-4-piperidyl)-amino] -6-(2-hydroxyethylamino)-1,3,5-triazine 12.0 g of 2-chloro-4,6-bis N-(2,2,6,6-tetramethyl-4-piperidyl)ethylamino] -1,3,5-triazine [obtained as described in Preparation 2(B)], 2.3 g of ethanolamine and 2.0 g of potassium carbonate in 50 ml of dioxane, were heated under reflux for 5 hours. At the end of this time, the dioxane was removed by distillation under reduced pressure, and a mixture of ethyl acetate and water was added thereto, after which the mixture was shaken. The ethyl acetate layer was separated, dried and concentrated by evaporation under reduced pressure, and the resulting residue was recrystallized from ethyl acetate to yield 11.6 g of the title compound as crystals melting at 184° to 185° C.

Preparations 3(B) to 3(H)

A procedure similar to that described in Preparation 3(A) was repeated, except that the corresponding chlorotriazine compound and corresponding amino compound or alcohol compound were employed, to give the following compounds:

3(B) 2,4-Bis[N-ethyl-N-(2,2,6,6-tetramethyl-4-piperidyl)amino] -6-(2-hydroxyethoxy)-1,3,5-triazine, melting at 192° to 193° C.:

3(C) 2,4-Bis[N-ethyl-N-(2,2,6,6-tetramethyl-4-piperidyl)amino] -6-[2-(2-hydroxyethoxy)ethoxy]-1,3,5-triazine, melting at 127° to 128° C.:

3(D) 2,4-Bis[N-butyl-N-(2,2,6,6-tetramethyl-4-piperidyl)amino] -6-(2-hydroxyethylamino)-1,3,5-triazine, melting at 130° to 132° C.:

3(E) 2,4-Bis[N-butyl-N-(2,2,6,6-tetramethyl-4-piperidyl amino]-6-(2-hydroxyethoxy)-1,3,5-triazine, melting at 157° to 159° C.;

3(F) 2,4-Bis[N-butyl-N-(2,2,6,6-tetramethyl-4-piperidyl)amino] -6-(3-hydroxypropylamino)-1,3,5triazine, melting at 150° to 152° C.:

3(G) 2,4-Bis[N-butyl-N-(2,2,6,6-tetramethyl-4-piperidyl)amino] -6-[N-(2-hydroxyethyl)-N-methylamino]1,3,5-triazine, melting at 75° C.;

3(H) 2,4-Bis[N-methyl-N-(2,2,6,6-tetramethyl-4-piperidyl)amino] -6-(2-hydroxyethylamino)-1,3,5-triazine, melting at 166° to 168° C.

PREPARATION 4

4(A) Ethyl N-(2,4-dichloro-1,3,5-triazin-6-yl)-glycinate 36.9 g of cyanuric chloride, 27.9 g of ethyl glycinate hydrochloride and 33.6 g of sodium bicarbonate were heated under reflux in 200 ml of dioxane for 30 minutes. At the end of this time, the dioxane was removed by distillation under reduced pressure, and a mixture of ethyl acetate and water was added to the resulting residue, after which the mixture was shaken.

The ethyl acetate layer was separated, dried and concentrated by evaporation under reduced pressure, and the resulting residue was recrystallized from a mixture of hexane and ethyl acetate, to yield 45.0 g of the title compound as crystals melting at 82° to 87° C.

4(B) Methyl
2-[N-(2,4-dichloro-1,3,5-triazin-6-yl)]-amino-2-methylpropiopate

A procedure similar to that described in Preparation 4(A) was repeated, except that the ethyl glycinate was replaced by methyl 2-amino-2-methylpropionate, to produce the title compound, melting at 114° to 119° C.

4(C) Ethyl
N-[2,4-bis(N-butyl-N-(2,2,6,6-tetramethyl-4-piperidyl)-
amino) -1,3,5-triazin-6-yl]glycinate 2.36 g of ethyl N-(2,4-dichloro-1,3,5-triazin-6-yl)glycinate [obtained as described in Preparation 4(A)], 4.19 g of 2,2,6,6-tetramethyl-4-(butylamino)piperidine [obtained as described in Preparation i(A)] and 2.77 g of sodium bicarbonate were heated under reflux in 20 ml of xylene for 29 hours. At the end of this time, the xylene was removed by distillation under reduced pressure, and a mixture of methylene chloride and water was added to the resulting residue, after which the mixture was shaken. The methylene chloride layer was separated, dried and concentrated by evaporation under reduced pressure, and the resulting residue was purified by silica gel column chromatography (using a 20:10:1:1 by volume mixture of hexane, diethyl ether, ethanol and triethylamine as eluent), to yield 5.46 g of the title compound melting at 40° C.

Preparations 4(D) to 4(F)

A procedure similar to that described in Preparation 4(C) was repeated, except that the appropriate starting materials were employed, to obtain the following:

4(D) Ethyl N-[2,4-bis(N-methyl-N-(2,2,6,6-tetramethyl-4-piperidyl)amino) -1,3,5-triazin-6-yl]glycinate, melting at 133° to 136° C., using 2,2,6,6-tetramethyl-4-(methylamino)piperidine in place of 2,2,6,6-tetramethyl-4-(butylamino)piperidine;

4(E) Ethyl N-[2,4-bis(N-ethyl-N-(2,2,6,6-tetramethyl-4-piperidyl)amino) -1,3,5-triazin-6-yl]glycinate, melting at 125° to 129° C., using 2,2,6,6-tetramethyl-4-(ethylamino)piperidine in place of 2,2,6,6-tetramethyl-4(butylamino)piperidine;

4(F) Methyl 2-[N-(2,4-bis(N-ethyl-N-(2,2,6,6-tetramethyl-4-piperidyl)amino) -1,3,5-triazin-6-yl]-amino-2-methylpropionate, melting at 231° to 232° C., using methyl 2-[N-(2,4-dichloro-1,3,5-triazin-6-yl)]-amino-2-methylpropionate [obtained as described in Preparation 4(B)] and 2,2,6,6-tetramethyl-4-(ethylamino)piperidine [obtained as described in Preparation i(B)].

4(G) Methyl
N-[2,4-bis[N-methyl-N-(2,2,6,6-tetramethyl-4-piperidyl)amino] -1,3,5-triazin-6-yl}alanate 3.69 g of cyanuric chloride, 2.79 g of methyl DL-alanate hydrochloride and 3.36 g of sodium bicarbonate were heated under reflux for one hour in 100 ml of dioxane. At the end of this time, the dioxane was removed by distillation under reduced pressure. A mixture of ethyl acetate and water was added to the residue, and the resulting mixture was shaken. The ethyl acetate layer was separated, dried and concentrated by evaporation under reduced pressure. The resulting residue, 6.80 g of 2,2,6,6-tetramethyl-4-(methylamino)piperidine [obtained as described in Preparation 1(C)] and 3.36 g of sodium bicarbonate were heated under reflux in 100 ml of xylene for 4 hours. At the end of this time, the xylene was removed by distillation under reduced pressure. To the residue was added a mixture of methylene chloride and water, and then the mixture was shaken. The methylene chloride layer was separated, dried and concentrated by evaporation under-reduced pressure. The residue was purified by silica gel column chromatography (using a 5:1:1 by volume mixture of ethyl acetate, ethanol and triethylamine as eluent) to afford 8.03 g of the title compound melting at 140° to 141° C.

4(H) Methyl
6-N-(2,4-dichloro-1,3,5-triazin-6-yl)-aminohexanoate 2.26 g of c-caprolactam and 2 g of 35% v/v aqueous hydrochloric acid were heated under reflux for 20 hours in 5 ml of methanol. At the end of this time, the methanol was removed by distillation under reduced pressure, resulting in 1.84 g of a residue. The whole of this residue, 1.84 g of cyanuric chloride and 1.7 g of sodium bicarbonate were then heated under reflux for 1 hour in 5 ml of dioxane. At the end of this time, the dioxane was removed by distillation under reduced pressure. A mixture of ethyl acetate and water was added to the residue, and the resulting mixture was shaken. The ethyl acetate layer was separated, dried and concentrated by evaporation under reduced pressure. The resulting residue was recrystallized from hexane to yield 1.50 g of the title compound, melting at 60° to 61° C.

4(I) Methyl
6-<N-{2,4-bis[N-butyl-N-(2,2,6,6-tetramethyl-4-piperidyl)amino]
-1,3,5-triazin-6-yl}amino>hexanoate 1.15 g of methyl 6-N-(2,4-dichloro-1,3,5-triazin-6-yl)aminonexanoate [prepared as described in Preparation 4(H) ], 2.2 g of 2,2,6,6-tetramethyl-4-butylaminopiperidine and 0.90 g of sodium bicarbonate were healed under reflux for 20 hours in 10 ml of xylene. At the end of this time, the xylene was removed by distillation under reduced pressure. A mixture of ethyl acetate and water was added to the residue, and the resulting mixture was shaken. The ethyl acetate layer was separated, dried and concentrated by evaporation under reduced pressure. The resulting residue was purified by silica gel column chromatography (using a 28:1:1 by volume mixture of ethyl acetate, ethanol and triethylamine as eluent), to yield 1.15 g of the title compound, melting at 48° C.

EXAMPLE 50

100 parts of unstabilized polypropylene powder (melt flow rate=10 to 15), 0.3 part of stearyl 3-(3,5-di-t-butyl-4-hydroxyphenyl) propionate (an antioxidant) and 0.25 part of one of the stabilizers of this invention were kneaded together in a Brabender Plasti-Corder at 200° C. for 10 minutes to obtain a homogeneous composition. The resulting mass was pressed into a sheet having a thickness of 2 to 3 mm using a laboratory press. Portions of this sheet were pressed by a hydraulic press at 260° C. for 6 minutes, and immediately thereafter it was introduced into cold water Lo obtain a sheet having a thickness of 0.5 mm. The same procedures were followed to form a film having a thickness of 0.i mm from the 0.5 mm thick sheet, and the resulting film was cut into test pieces having dimensions of 50 mm×120 min.

The test pieces were exposed to light in a sunshine carbon weather meter at a black panel temperature of 63 ±3° C. The exposed test specimens were subjected to periodic tensile tests, and the "deterioration time" was obtained by determining the time when the elongation of each specimen droped to 50% of its initial value. The test results are shown as the ratio between the deterioration time of the stabilizer of this invention and that of a control specimen to which the stabilizer of this invention had not been added.

These results are summarized in the following Table 2, wherein the compounds are identified by the numbers hereinbefore assigned to them.

The 2 prior art compounds also tested are:

A: ethylene glycol bis N-methyl-N-(1,2,2,6,6-pentamethyl-4-piperidyl)aminoacetate]: and
B: 1,6-bis{[N-methyl-N-(1,2,2,6,6-pentamethyl-4-piperidyl)amino] acetatamido}hexane.

TABLE 2

| Compound No. | Light resistance (ratio) |
|---|---|
| 23 | 6.3 |
| 27 | 6.4 |
| 29 | 6.5 |
| 33 | 6.8 |
| 34 | 7.0 |
| 46 | 6.1 |
| 49 | 6.6 |
| 50 | 6.3 |
| 57 | 6.6 |
| 58 | 5.9 |
| 59 | 6.1 |
| 62 | 6.4 |
| 64 | 6.3 |
| 85 | 6.7 |
| 86 | 5.6 |
| 105 | 7.0 |
| 114 | 7.0 |
| A | 4.7 |
| B | 5.3 |
| Control (no stabilizer) | 1.0 |

EXAMPLE 51

Test pieces of dimensions 10 mm×100 mm were prepared from the 0.5 mm thick polypropylene sheet obtained as described in Example 50. They were kept in an oven at 150° C. and regularly observed. The number of days before the test pieces became white through brittleness was noted and is reported in Table 3.

TABLE 3

| Compound No. | Days to brittleness |
|---|---|
| 23 | 30 |
| 27 | 59 |
| 29 | 60 |
| 33 | 31 |
| 34 | 54 |
| 46 | 30 |
| 49 | 135 |
| 50 | 128 |
| 57 | 33 |
| 58 | 30 |
| 59 | 30 |
| 62 | 38 |
| 64 | 69 |
| 85 | 38 |
| 86 | 25 |
| 105 | 77 |
| 114 | 55 |
| A | 9 |
| B | 13 |
| Control (no stabilizer) | 5 |

We claim:

1. A polymer composition comprising a polymer stabilized against the effects of light and heat by the incorporation of a polymer stabilizer, wherein the polymer stabilizer comprises at least one compound selected from the group consisting of compounds of formula (I):

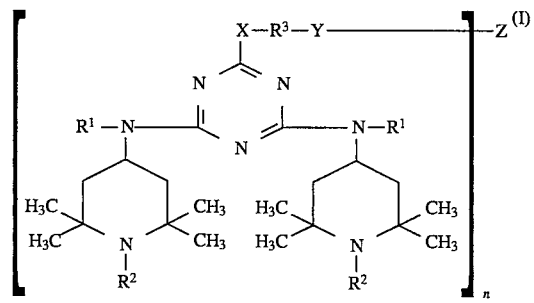

wherein:

R represents a hydrogen atom, an alkyl group having from 1 to 18 carbon atoms, an alkoxyalkyl group having from 3 to 22 carbon atoms, a carboxylic acyl group having from 2 to 18 carbon atoms, a phenylalkyl group in which the alkyl part has from 1 to 4 carbon atoms and in which the phenyl part is unsubstituted or has at least one substituent selected from the group consisting of $C_1$–$C_4$ alkyl groups, $C_1$–$C_4$ alkoxy groups and halogen atoms, or a group of formula (II):

wherein $R^4$ has the same meaning as defined below for 2;

R² represents a hydrogen atom, an alkyl group having from 1 to 18 carbon atoms, a carboxylic acyl group having from 2 to 18 carbon atoms or a phenylalkyl group in which the alkyl part has from 1 to 4 carbon atoms and in which the phenyl part is unsubstituted or has at least one substituent selected from the group consisting of $C_1$–$C_4$ alkyl groups, $C_1$–$C_4$ alkoxy groups and halogen atoms;

R³ represents an alkylene group having from 1 to 6 carbon atoms or an alkylene group having from 1 to 6 carbon atoms which is interrupted by at least one oxygen atom;

X represents an oxygen atom or a group of formula —NR⁵—, wherein R⁵ represents a hydrogen atom or an alkyl group having from 1 to 4 carbon atoms;

Y represents a group of formula —OCO—, a group of formula —COO—, a group of formula —CONH— or a group of formula —OCONH—;

is an integer from 2 to 4; and when n is 2:

Z represents:

(i) an alkylene group having from 1 to 18 carbon atoms or an alkylene group having from 1 to 18 carbon atoms which is interrupted by at least one member selected from the group consisting of oxygen atoms, sulfur atoms and groups of formula (II'):

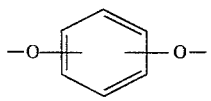
(II')

or (ii) a group of formula (III):

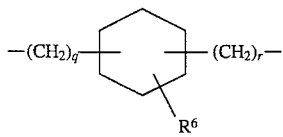
(III)

or (iii) a group of formula (IV):

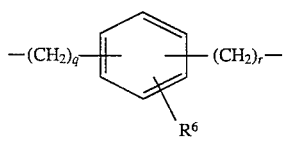
(IV)

or (iv) a group of formula (V):

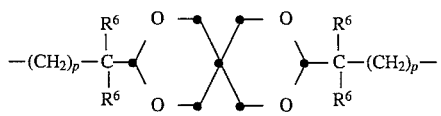
(V)

or (v) a group of formula (VI):

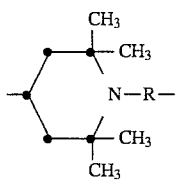
(VI)

wherein:

R⁶ represents a hydrogen atom or an alkyl group having from 1 to 4 carbon atoms;

R represents an alkylene group having from 2 to 4 carbon atoms;

p is an integer from 1 to 4; and q and r are independently selected from the group consisting of the cipher 0 and the integers from 1 to 3;

when n is 3:

Z represents an alkanetriyl group having from 3 to 8 carbon atoms or a group of formula (VII):

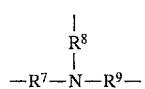
(VII)

wherein R⁷, R⁸ and R⁹ are independently selected from the group consisting of alkylene groups having from 1 to 5 carbon atoms, provided that the total number of carbon atoms in R⁷+R⁸+R⁹ is from 3 to 8;

or when n is 4:

Z represents an alkanetetrayl group having from 4 to 8 carbon atoms or an alkanetetrayl group having from 4 to carbon atoms which is interrupted by at least one oxygen atom;

and acid addition salts thereof.

2. The composition of claim 1, wherein:

R¹ represents a hydrogen atom, a $C_1$–$C_8$ alkyl group, an alkoxyalkyl group having a total of from 3 to 10 carbon atoms, an acetyl group, a benzyl group or a group of formula (II), as shown in claim 1, in which R⁴ represents a hydrogen atom, a $C_1$–$C_4$ alkyl group, an acetyl group or a benzyl group:

R² represents a hydrogen atom, a $C_1$–$C_4$ alkyl group, an acetyl group or a benzyl group:

R³ represents a $C_1$–$C_6$ alkylene group or a $C_1$–$C_6$ alkylene group interrupted by at least one oxygen atom:

X represents an oxygen atom or a group of formula —NH— or —NCH₃—:

Y represents a group of formula —OCO—, —CONH— or —COO—; and is 2 and Z represents a $C_1$–$C_{10}$ alkylene group, a $C_1$–$C_{10}$ alkylene group interrupted by at least one oxygen atom, a group of formula (V), as shown in claim 1, in which:

R⁶ represents a hydrogen atom or a methyl group; and p is 1 or 2, or a group of formula (VI), as shown in claim 1, in which:

R represents a $C_2$ or $C_3$ alkylene group.

3. The composition of claim 1, wherein:

R¹ represents a hydrogen atom, a $C_1$–$C_8$ alkyl group, an alkoxyalkyl group having a total of from 3 to 10 carbon atoms, an acetyl group, a benzyl group or a group of formula (II), as shown in claim 1, in which R⁴ represents a hydrogen atom, a $C_1$–$C_4$ alkyl group, an acetyl group or a benzyl group:

R² represents a hydrogen atom, a $C_1$–$C_4$ alkyl group, an acetyl group or a benzyl group;

R³ represents a $C_1$–$C_6$ alkylene group or a $C_1$–$C_6$ alkylene group interrupted by at least one oxygen atom;

X represents an oxygen atom or a group of formula —NH— or —NCH₃—;

Y represents a group of formula —OCO—, —CONH— or —COO—: and n is 3 and Z represents a $C_3$–$C_6$ alkanetriyl group or a group of formula (VII), as shown in claim 1, in which: R⁷, R⁸ and R⁹ are independently selected from the group consisting of alkylene groups having from 1 to 4 carbon atoms, provided that the total number of carbon atoms in R⁷+R⁸+R⁹ is from 3 to 6.

4. The composition of claim 1, wherein:

$R^1$ represents a hydrogen atom, a $C_1-C_8$ alkyl group, a benzyl group or a group of formula (II), as shown in claim 1 in which $R^4$ represents a hydrogen atom, a methyl group or a benzyl group;

$R^2$ represents a hydrogen atom, a methyl group or a benzyl group;

$R^3$ represents a $C_1-C_4$ alkylene group or a $C_1-C_4$ alkylene group interrupted by at least one oxygen atom;

X represents an oxygen atom or a group of formula —NH— or —NCH$_3$—;

Y represents a group of formula —OCO—, —CONH— or —COO—; and n is 2 and Z represents a $C_1-C_{10}$ alkylene group, a $C_1-C_{10}$ alkylene group interrupted by at least one oxygen atom, a group of formula (V), as shown in claim 1, in which: $R^6$ represents a hydrogen atom or a methyl group; and p is 1 or 2, or a group of formula (VI), as shown in claim 1, in which: R represents a $C_2$ or $C_3$ alkylene group.

5. The composition of claim 1, wherein:

$R^1$ represents a hydrogen atom or a $C_1-C_4$ alkyl group;

$R^2$ represents a hydrogen atom or a methyl group:

$R^3$ represents a $C_1-C_2$ alkylene group;

X represents a group of formula —NH— or —NCH$_3$—;

Y represents a group of formula —OCO—, —CONH— or —COO—; and n is 2 and Z represents a $C_2-C_8$ alkylene group or a $C_2-C_8$ alkylene group interrupted by at least one oxygen atom.

6. The composition of claim 1, wherein said polymer stabilizer is selected from the group consisting of:

Bis{2-(2,4-bis N-ethyl-N-(2,2,6,6-tetramethyl-4-piperidyl)amino] -1,3,5-triazin-6-yl)aminoethyl}succinate:

Bis {2-(2,4-bis[N-ethyl-N-(2,2,6,6-tetramethyl-4-piperidyl)amino] -1,3,5-triazin-6-yl)aminoethyl}sebacate;

Ethylene glycol bis{N-(2,4-bis N-ethyl-N-(2,2,6,6-tetramethyl-4-piperidyl)amino] -1,3,5-triazin-6-yl)glycinate}:

Butane-1,4-diol bis{N-(2,4-bis N-ethyl-N-(2,2,6,6-tetramethyl-N-piperidyl)amino] -1,3,5-triazin-6-yl)glycinate}:

Bis{2-(2,4-bis(N-butyl-N-(2,2,6,6-tetramethyl-4-piperidyl)amino] -1,3,5-triazin-6-yl)aminoethyl}adipate:

Bis{2-(2,4-bis N-butyl-N-(2,2,6,6-tetramethyl-4-piperidyl)amino] -1,3,5-triazin-6-yl)aminoethyl}sebacate;

Hexane-1,6-diol bis{N-(2,4-bis N-methyl-N-(2,2,6,6-tetramethyl-4-piperidyl)amino] -1,3,5-triazin-6-yl)glycinate}; and Diethylene glycol bis{N-(2,4-bis N-ethyl-N(2,2,6,6-tetramethyl-4-piperidyl)amino] -1,3,5-triazin-6-yl)glycinate};

and acid addition salts thereof.

7. The composition of claim 14, wherein said polymer is a synthetic polymer.

8. The composition of claim 14, wherein said polymer is selected from the group consisting of olefin and diene polymers, styrene polymers, halogen-containing polymers, polymers which are derived from $\alpha,\beta$-unsaturated acids and their derivatives, polymers which are derived from unsaturated alcohols and amines or their acyl derivatives or acetals, epoxy polymers, polyacetals, polyalkylene oxides and polyphenylene oxides, polyurethanes and polyureas, polycarbonates, polysulfones, polyamides and copolyamides, polyesters, crosslinked polymers, alkyd resins and unsaturated polyester resins.

9. The composition according to claim 1, wherein $R^1$ is a $C_1-C_4$ alkyl group, $R^2$ is a hydrogen, $R^3$ is a $C_1-C_2$-alkylene group, X is —NH—, Y is —OCO— or —COO—, n is 2, and Z is a $C_2-C_8$ alkylene group or a $C_2-C_8$ alkylene group interrupted by one oxygen atom and n is 2.

10. The composition according to claim 1, wherein $R^1$ is methyl, ethyl or butyl, $R^2$ is hydrogen, $R^3$ is a $C_1-C_2$-alkylene group, X is —NH—, Y is —OCO— or —COO—, n is 2 and Z is a $C_2-C_8$ alkylene group or a $C_2-C_8$-alkylene group interrupted by an oxygen.

* * * * *

UNITED STATES PATENT AND TRADEMARK OFFICE
CERTIFICATE OF CORRECTION

PATENT NO. : 5,486,556
DATED : January 23, 1996
INVENTOR(S) : TODA et al

It is certified that error appears in the above-indentified patent and that said Letters Patent is hereby corrected as shown below:

Column 15, line 62, replace "$R^{3'}$" with --$R^3$--.

Column 33, line 19 (Claim 1): insert --n-- before "is".

Column 34, line 38 (Claim 2): insert --n-- before "is".

Column 36, line 11 (Claim 7): replace "14" with --1--.

Column 36, line 13 (Claim 8): replace "14" with --1--.

Signed and Sealed this

Twenty-first Day of July, 1998

Attest:

*Attesting Officer*

BRUCE LEHMAN

*Commissioner of Patents and Trademarks*